(12) United States Patent
Adibhatla Kali Satya et al.

(10) Patent No.: US 9,481,655 B2
(45) Date of Patent: *Nov. 1, 2016

(54) 6,7-DIALKOXY QUINAZOLINE DERIVATIVES AND METHODS OF TREATING DRUG RESISTANT AND OTHER TUMORS

(71) Applicant: Natco Pharma Limited, Hyderabad, Andhra Pradesh (IN)

(72) Inventors: Bhujanga rao Adibhatla Kali Satya, Andhra Pradesh (IN); Ramanadham Jyothi Prasad, Andhra Pradesh (IN); Bollepalli Nageshwara Rao, Andhra Pradesh (IN); Nannapaneni Venkaiah Chowdary, Andhra Pradesh (IN)

(73) Assignee: NATCO PHARMA LIMITED, Banjara Hills, Hyderabad, Andhra Pradesh (IN)

( * ) Notice: Subject to any disclaimer, the term of this patent is extended or adjusted under 35 U.S.C. 154(b) by 0 days.

This patent is subject to a terminal disclaimer.

(21) Appl. No.: 14/583,286

(22) Filed: Dec. 26, 2014

(65) Prior Publication Data

US 2015/0141421 A1 May 21, 2015

Related U.S. Application Data

(60) Division of application No. 12/833,789, filed on Jul. 9, 2010, now Pat. No. 8,921,362, which is a continuation-in-part of application No. PCT/IN2008/000036, filed on Jan. 18, 2008.

(60) Provisional application No. 61/225,419, filed on Jul. 14, 2009, provisional application No. 61/225,425, filed on Jul. 14, 2009.

(51) Int. Cl.
*A61K 31/496* (2006.01)
*A61K 31/517* (2006.01)
*C07D 239/94* (2006.01)

(52) U.S. Cl.
CPC ............... *C07D 239/94* (2013.01)

(58) Field of Classification Search
None
See application file for complete search history.

(56) References Cited

U.S. PATENT DOCUMENTS 5,183,884 A   2/1993  Kraus et al.
5,332,671 A   7/1994  Ferrara et al.
(Continued)

FOREIGN PATENT DOCUMENTS

EP   0 520 722 A1   12/1992
EP   0 566 226 A1    1/1993
(Continued)

OTHER PUBLICATIONS

"Structure-Activity Relationship and Drug Design." Remington's Pharmaceutical Scienes (Sixteenth Edition). Mack Publishing. 1980. pp. 420-425.*

(Continued)

*Primary Examiner* — Anna Pagonakis
(74) *Attorney, Agent, or Firm* — Mintz, Levin, Cohn, Ferris, Glovsky and Popeo, P.C.

(57) ABSTRACT

Methods of inhibiting a receptor tyrosine kinase in a subject in need thereof. Methods of inhibiting the growth of a tumor cell in a subject in need thereof. Methods of treating pancreatic cancer in a subject in need of treatment for pancreatic cancer. Methods of treating HER2 positive breast cancer in a subject in need of treatment for HER2 positive breast cancer. Methods of treating drug resistant non-small cell lung cancer in a subject in need of treatment for drug resistant non-small cell lung cancer. Each of these methods can include administering to the subject an effective amount of a compound of formula (I) or a pharmaceutically acceptable salt thereof.

2 Claims, 12 Drawing Sheets

Western blot analysis of A549 cells treated with erlotinib HCl and NRC 2694. Dose dependent decrease in EGFR levels was observed.

(56) References Cited

U.S. PATENT DOCUMENTS

| | | | |
|---|---|---|---|
| 5,457,105 | A | 10/1995 | Barker |
| 5,475,001 | A | 12/1995 | Barker |
| 5,616,582 | A | 4/1997 | Barker |
| 5,747,498 | A | 5/1998 | Schnur et al. |
| 5,770,599 | A | 6/1998 | Gibson |
| 5,811,098 | A | 9/1998 | Plowman et al. |
| 6,900,221 | B1 | 5/2005 | Norris et al. |
| 8,921,362 | B2 * | 12/2014 | Adibhatla Kali Satya ............... C07D 239/94 514/234.5 |
| 2007/0020261 | A1 | 1/2007 | Sliwkowski et al. |

FOREIGN PATENT DOCUMENTS

| | | |
|---|---|---|
| EP | 0 602 851 A1 | 12/1993 |
| EP | 0 635 498 A1 | 7/1994 |
| EP | 0 635 507 A1 | 7/1994 |
| WO | WO 96/30347 | 10/1996 |
| WO | WO 2005/070909 A1 | 8/2005 |
| WO | WO 2006/090413 A1 | 8/2006 |
| WO | WO 2007/060691 A2 | 5/2007 |

OTHER PUBLICATIONS

Berge et al. "Pharmaceutical Salts." Journal of Pharmaceutical Salts, 66(1), 1977: 1-19.*

Bradshaw, T.K., "Cell transformation: The role of oncogenes and growth factors," *Mutagenesis* (1986) 1 (2): 91-97.

Larsen, E.R., "New approaches to antitumor therapy," *Annual Reports in Medicinal Chemistry* (1989) 24 (13): 121-128.

Cohen et al., "Epidermal growth factor receptor as a therapeutic target in colorectal cancer," *Clinical Colorectal Cancer* (2003) 2 (4): 246-251.

Arteaga, C. L., "ErbB-targeted therapeutic approaches in human cancer," *Experimental Cell Research* (2003) 284: 122-130.

Hunter, T., "A thousand and one protein kinases," *Cell* (1987) 50: 823-829.

Gullick, W.J., "Prevalence of aberrant expression of the epidermal growth factor receptor in human cancers," *British Medical Bulletin* (1991) 47 (1): 87-98.

Sainsbury et al., "Epidermal growth factor receptor status of histological sub-types of breast cancer," *Br. J. Cancer* (1988) 58: 458-460.

Baselga et al., "HER-targeted tyrosine-kinase inhibitors," *Oncology* (2002) 63: 6-16.

Bolen et al., "Analysis of pp60c-src in human colon carcinoma and normal human colon mucosal cells," *Oncogene Research* (1987) 1: 149-168.

Parkinson et al., "An inhibitor of the epidermal growth factor receptor function does not affect the ability of human papillomavirus 11 to form warts in the xenografted immunodeficient mouse model," *Antiviral Research* (2007) 74: 43-50.

Chapman, M.S., "Pharmaceutical combinations comprising RDEA119/Bay 869766 for the treatment of specific cancers," *Capulus an* (2010): 1161398.

Arteaga et al., "Clinical trial design and end points for epidermal growth factor receptor-targeted therapies: Implications for drug development and practice," *Clinical Cancer Research* (2003) 9: 1579-1589.

Tarceva (2011) <http://www.gene.com/gene/products/information/oncology/tarceva>.

Fischer et al., "Targeting receptor tyrosine kinase signaling in small cell lung cancer (SCLC): What have we learned so far?" *Cancer Treatment Reviews* (2007) 33: 391-406.

Arbiser et al., "Why targeted therapy hasn't worked in advanced cancer," *The Journal of Clinical Investigation* (2007) 117 (10): 2762-2765.

Madhusudan et al., "Tyrosine kinase inhibitors in cancer therapy," *Clinical Biochemistry* (2004) 37: 618-635.

Kwak et al., "Irreversible inhibitors of the EGF receptor may circumvent acquired resistant to gefitinib," *PNAS* (May 24, 2005) vol. 102, No. 21: 7665-7670.

* cited by examiner

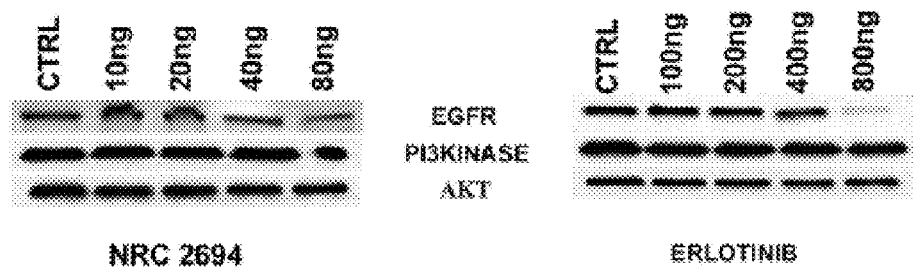
Figure-1: Western blot analysis of A549 cells treated with erlotinib HCl and NRC 2694. Dose dependent decrease in EGFR levels was observed.

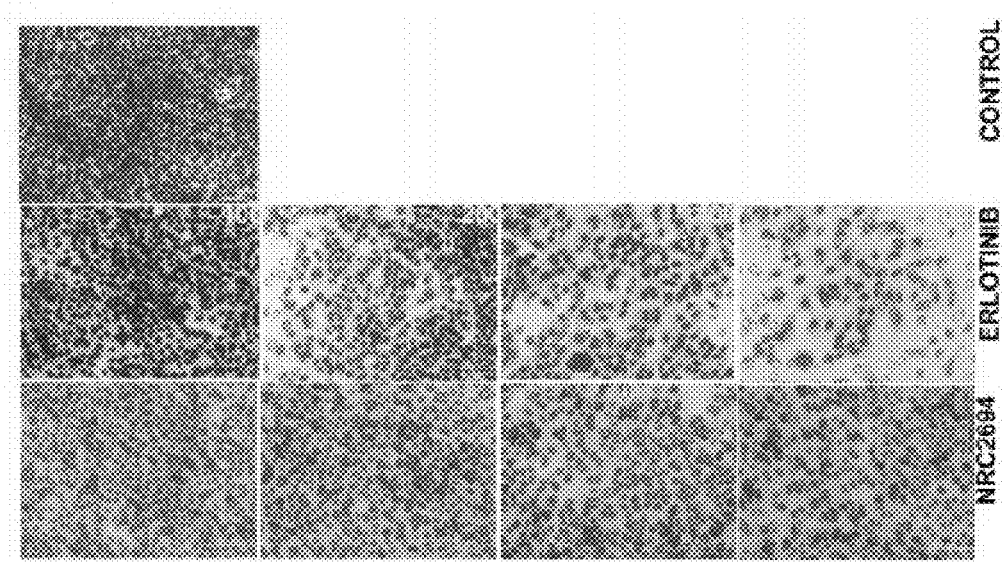
Figure-2: Matrigel invasion assay of H1299 cells treated with Erlotinib and NRC 2694. A dose dependent decrease in invasion was observed

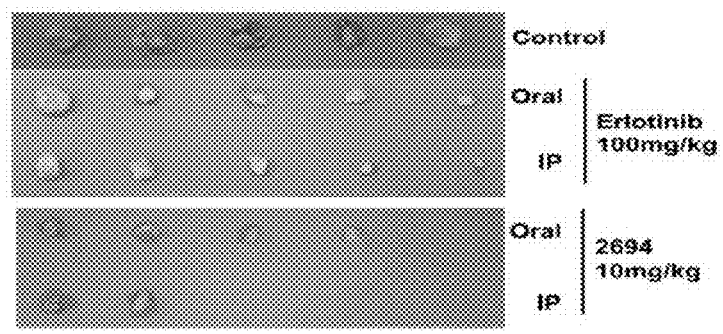
Figure-3: Decrease in tumor size induced by oral and ip administration of Erlotinib HCl and NRC 2694 in nude mice implanted with A549 human lung tumors

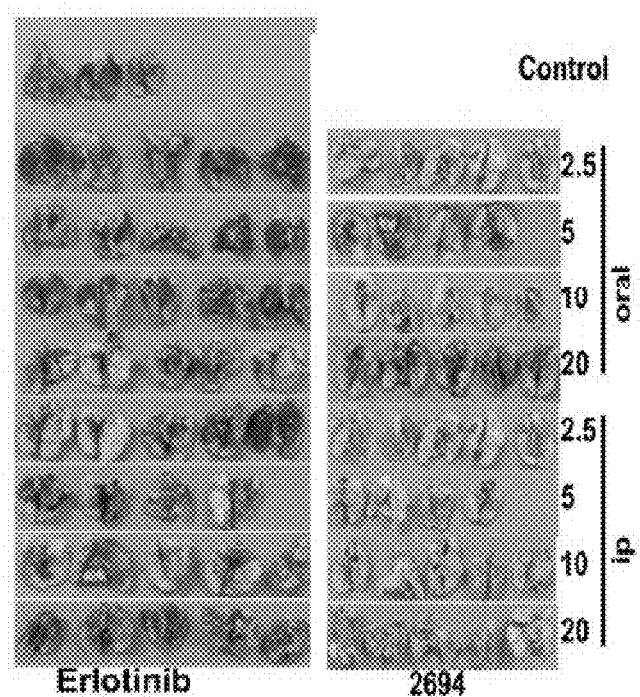
Figure-4: Lungs harvested from nude mice with A549 luciferase expressing cells treated with various concentrations of Erlotinib HCl and NRC 2694 by oral or ip routes

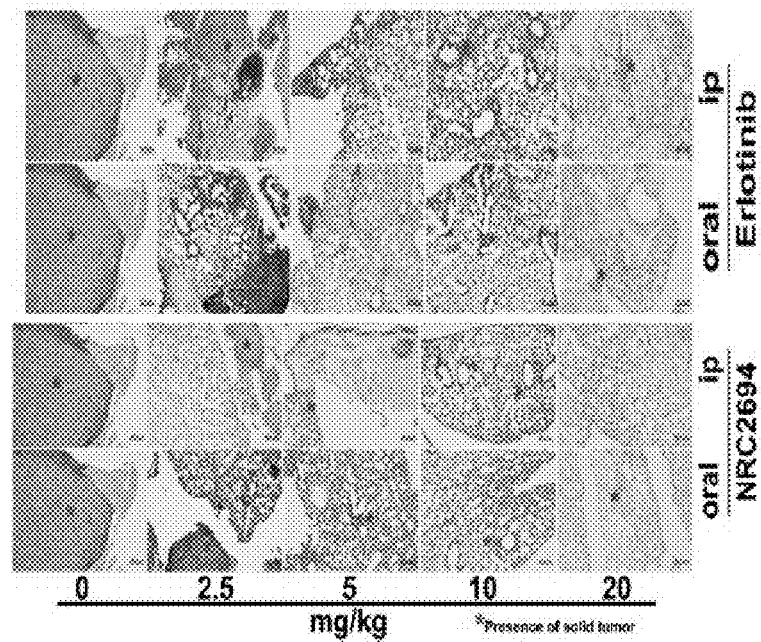
Figure-5: Representative H&E stained sections of nude mice tumor bearing lungs after treatment with Erlotinib HCl and NRC 2694

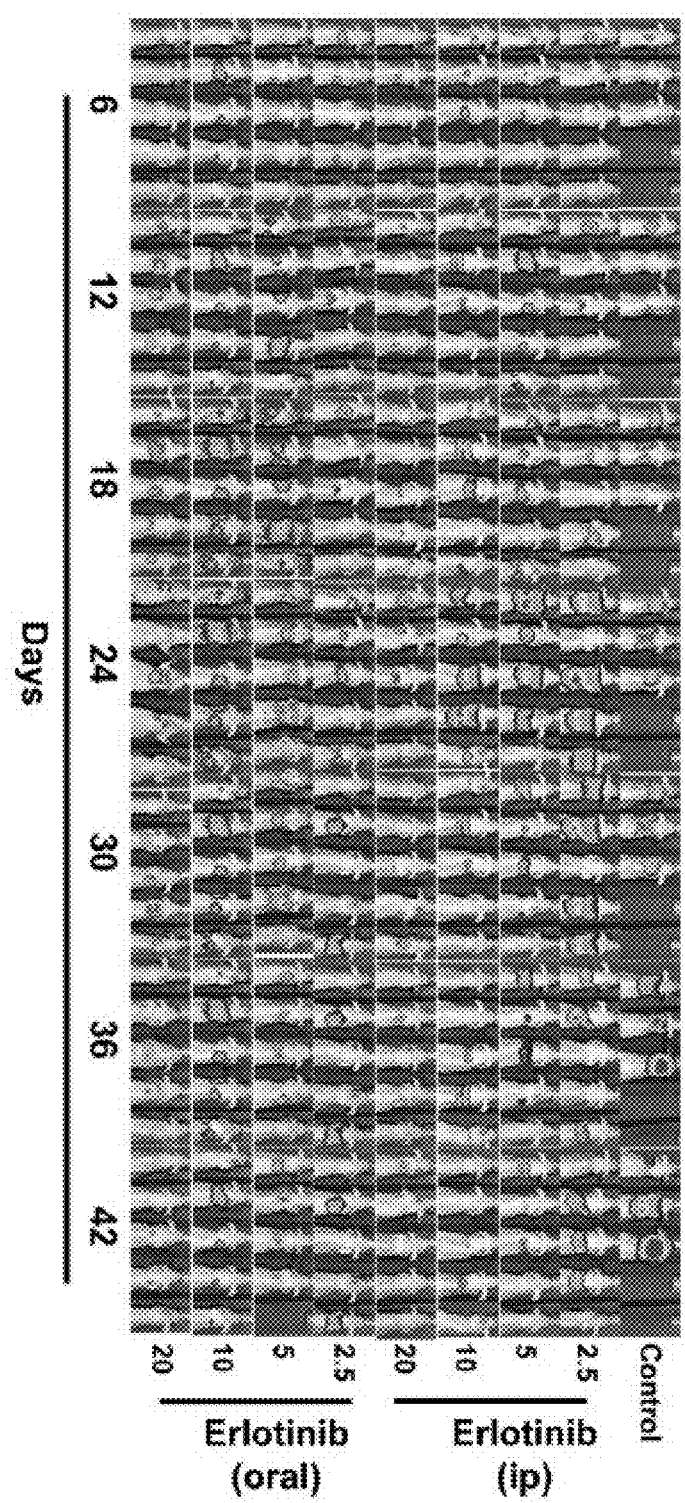
Figure-6: Nude mice implanted with A549 luciferase expressing cells treated with various concentrations of erlotinib HCl by oral and ip routes

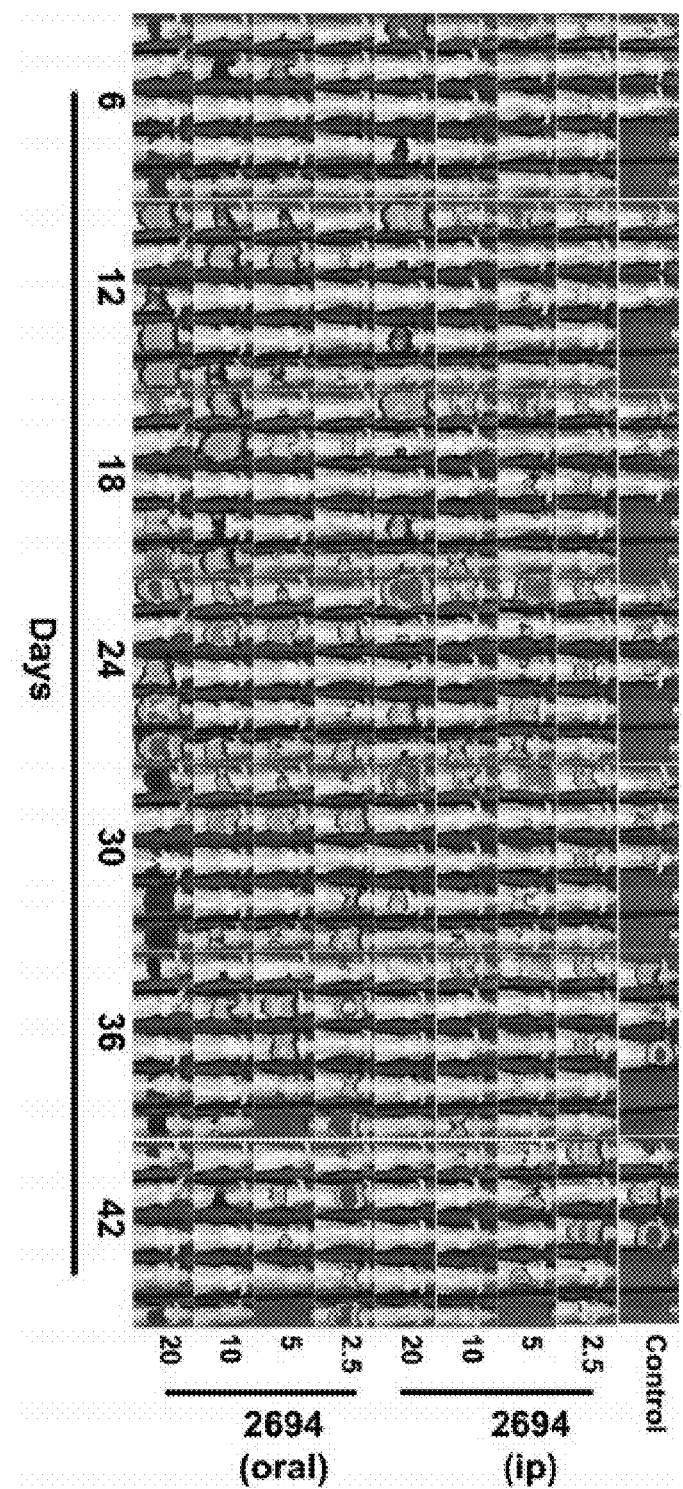
Figure-7: Nude mice implanted with A549 luciferase expressing cells treated with various concentrations of NRC 2694 by oral and ip routes

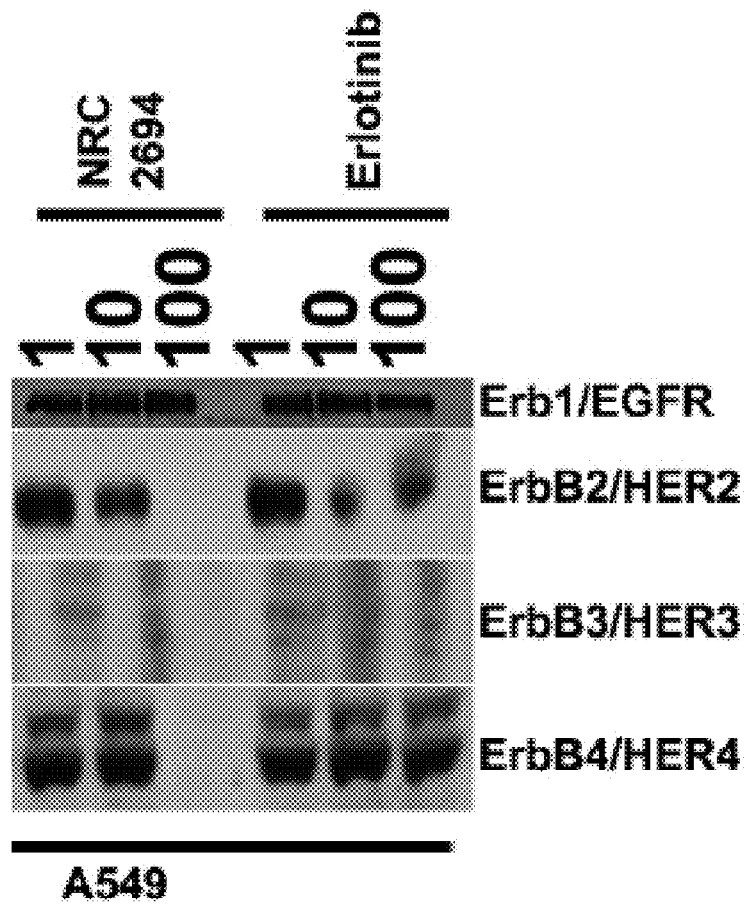
Figure-8: Study of the effect of NRC NCEs in relation to other receptors such as HER-1,2,3,4 and VEGFR *in vitro*
Decrease in levels of Erb1, ErbB2, ErbB3 and ErbB4 after treatment with NRC 2694 in A549 cells was observed

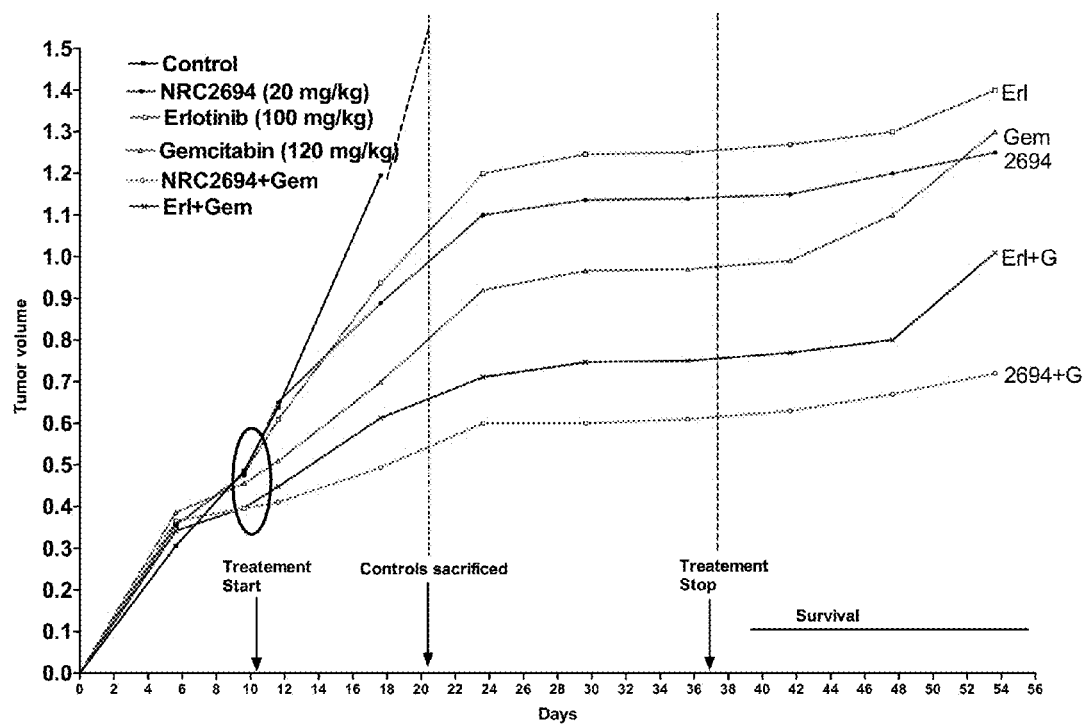
Figure No.9: Anticancer activity of NRC 2694 (Pancreatic cancer)

Figure No.10. Immunohistochemical Analysis of Pancreatic Tumor Sections (Anti-angiogenic activity)
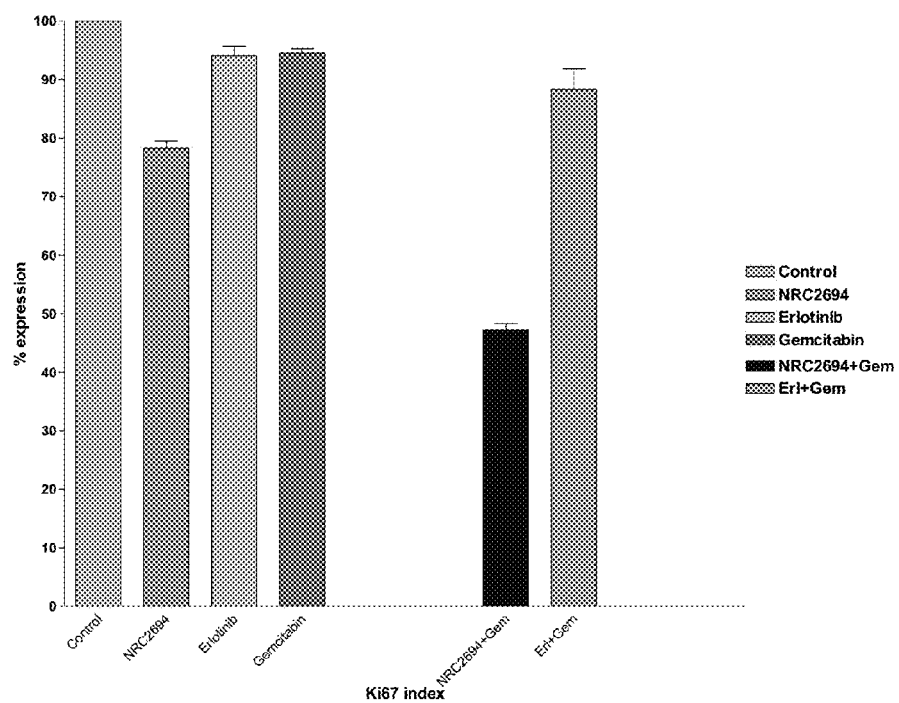

Figure No.11: NRC-2694 in Her-2 Positive Breast Cancer
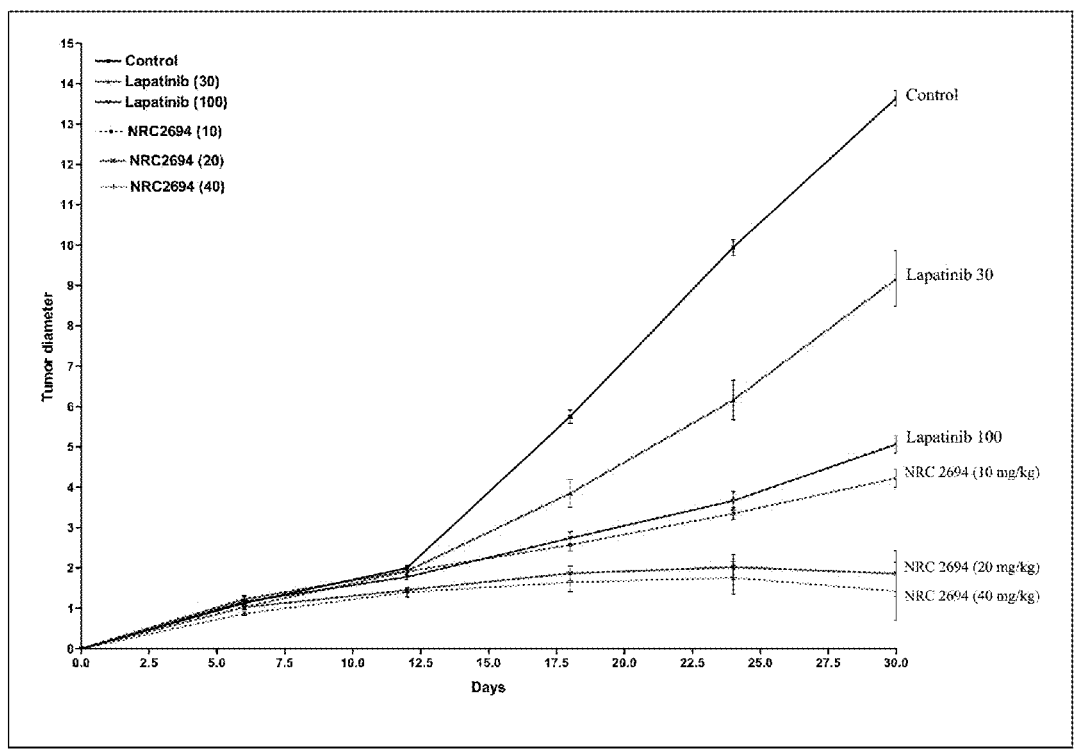

Figure No. 12: Anticancer activity of NRC 2694 for in Erlotinib/Gefitinib Resistant NSCLC
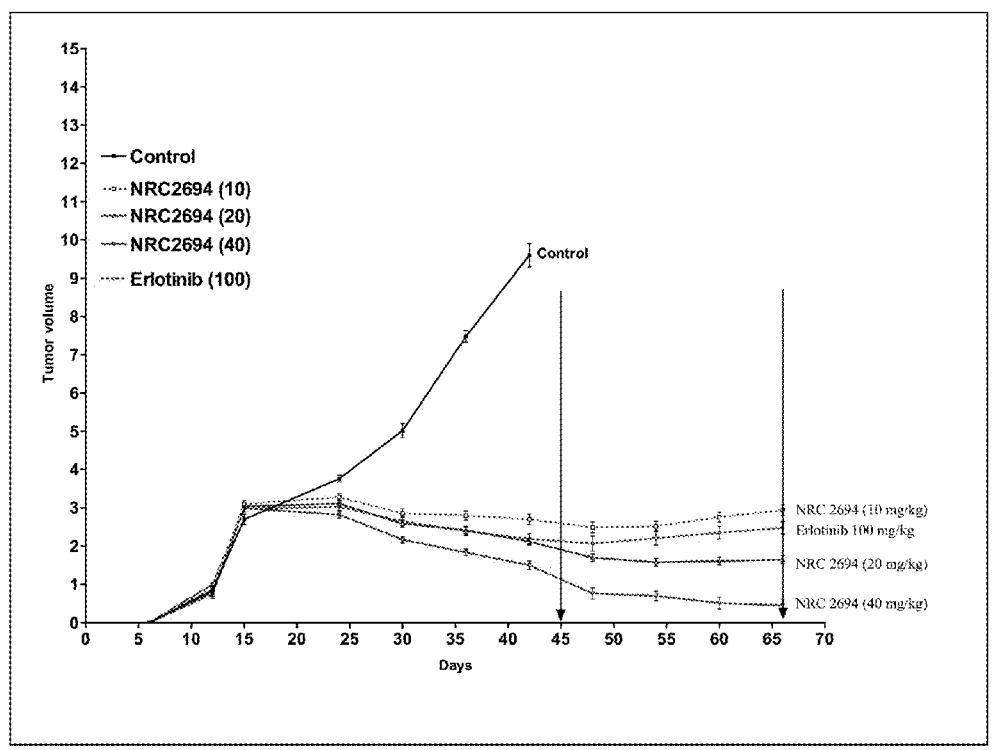

6,7-DIALKOXY QUINAZOLINE DERIVATIVES AND METHODS OF TREATING DRUG RESISTANT AND OTHER TUMORS

CROSS-REFERENCE TO RELATED APPLICATIONS

This application is a Divisional Application of U.S. patent application Ser. No. 12/833,789, filed Jul. 9, 2010, which is a Continuation-in-Part of International Application PCT/IN2008/000036, filed Jan. 18, 2008, and also claims priority to Ser. No. 61/225,419, filed Jul. 14, 2009 in the United States, and Ser. No. 61/225,425, filed Jul. 14, 2009 in the United States, and which applications are incorporated herein by reference.

FIELD OF THE INVENTION

The invention relates to 6,7-dialkoxy quinazoline derivatives, or pharmaceutically acceptable salts thereof, which possess anti-cancer activity and hence useful in methods of treatment in humans. The invention also relates to processes for the manufacture of the said quinazoline derivatives, and pharmaceutical compositions containing them.

BACKGROUND OF THE INVENTION

Most of the treatment regimes of the past for cell proliferation diseases such as psoriasis and cancer utilize compounds which inhibit DNA synthesis. Such compounds are toxic to cells and their beneficial effects can be derived when they show selectivity to tumor cells. In recent years it has been discovered that a cell may become cancerous by virtue of the transformation of a portion of its DNA into an oncogene, i.e., a gene which, on activation, leads to the formation of malignant tumour cells (Bradshas, Mutagenesis, 1986, 1: 91). Several oncogenes encode tyrosine kinase enzymes and certain growth factor receptors are also tyrosine kinase enzymes (Larsen et al., Ann. Reports in Med. Chem. 1989, Chapt. 13).

Receptor tyrosine kinases are important in the transmission of biochemical signals which initiate cell replication. They possess an extra cellular binding domain for growth factors such as an epidermal growth factor and an intracellular portion which functions as a kinase to phosphorylate tyrosine amino acids in proteins and hence to influence cell proliferation. Members of the ErbB family of receptor tyrosine kinases are mediators of cell growth, differentiation and survival that have been implicated in cancer. The receptors are over expressed in certain tumor cells. For example, it is known that such kinases are frequently present in common human cancers such as breast cancer (Saimbury et al., Brit, J. Cancer, 1988, 58: 458) and gastro intestinal cancers such colon, rectal and stomach cancers (Bolen et al., Oncogene Res., 1987, 1: 149). It was discovered that Tyrosine Kinase activity (TK activity) is more frequently detectable in malignant cells than in normal cells (Hunter, Cell, 1987, 50: 823).

More recently, it has been shown that Epidermal Growth Factor Receptor (EGFR) which possesses TK activity is over expressed in many human cancers such as brain, lung squamous cell, bladder, gastric, breast, head & neck, oesophageal, thyroid and the like. (W. J. Gullick, Brit. Med. Bull. 1991, 47: 87). The receptor family includes four distinct members, including epidermal growth factor receptor (EGFR or ErbB1), HER$^2$ (ErbB2 or p185$^{neu}$), HER3 (ErbB3) and HER4 (ErbB4 or tyro2). The HER (ErbB) family belongs to the subclass I receptor tyrosine kinase superfamily and consists of three distinct receptors, HER$^2$, HER3, and HER4. Sequences of these receptors can be found in U.S. Pat. No. 5,183,884 (erbB3/HER3); U.S. Pat. No. 5,811,098 (HER4/Erb4 receptor); erbB2/HER$^2$: Semba et al. (1985) Proc. Natl. Acad. Sci. USA 82:6497-6501 (designating the gene c-erbB-2); Coussens et al. (1985) Science 230:1132-1139 (designating the gene HER$^2$); or King et al. (1985) Science 229:974-976.

Another receptor tyrosine kinase that is associated with cancer is the VEGF (vascular endothelial growth factor) receptor, the sequence of which is disclosed in U.S. Pat. No. 5,332,671.

A strategy to inhibit EGFR-TK activity has been exploiting small synthetic molecules (Arteaga C L, Exp. Cell Res., 2003, 284: 122-130). Certain quinazoline derivatives like gefitinib (IRESSA®, Astra Zeneca), erlotinib (OSI-774, TARCEVA®), PD-183805, PKI-166, EKB-569, PD-168393, CGP-59362 have been have been investigated for possible treatment options for several forms of cancer (Baselga et al., Oncology 2002, 63: 6-16, Cohen R B., Clin. Colorectal Cancer, 2003, 2: 246-251). The European patent applications namely EP 0566226, EP0602851A1, EP 0635507 A1, EP 0635498 A1, EO 0520722 A1 disclose certain quinazoline derivatives possessing anti-cancer properties and that inhibit TK.

U.S. Pat. Nos. 5,475,001, 5,457,105, 5,616,582, 5,770,599, 5,747,498, and 6,900,221 disclose quinazoline derivatives with structural features such as a substituted anilino moiety in the 4-position and a variety of functionalized alkyl groups in the 6- and 7-positions of the quinazoline nucleus. Specifically U.S. Pat. Nos. 5,457,105, 5,616,582 disclose N-(3-Chloro-4-fluorophenyl)-7-methoxy-6-[3-(4-morpholinyl)propoxy]-4-quinazolinamine (Gefitinib) and U.S. Pat. Nos. 5,747,498 and 690,221 disclose N-(3-Ethylnylphenyl)-6,7-bis(2-methoxyethoxy)-4-quinazolinamine (Erlotinib). WO 20005/070909, WO 2007/060691 A$_2$ and WO 06/090413 disclose variations in synthesis or polymorphic forms of these two popular anti-cancer drugs.

Nonetheless, there remains a need for additional cancer therapies.

SUMMARY OF THE INVENTION

It has been surprisingly and unexpectedly found that quinazolines having a 3-Ethynyl anilino group at the 4-position and certain substituted alkoxy groups in the 6- and 7-positions have enhanced anti-proliferative properties when compared to other quinazoline anticancer agents. Also, surprisingly, the compounds of this invention are significantly less toxic and have a beneficial safety profile for therapeutic applications. The present quinazolines having a 3-Ethynyl anilino group at the 4-position and certain substituted alkoxy groups in the 6- and 7-positions are described by the general formula (I)

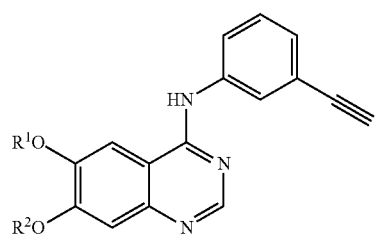

Formula I in which:
R¹ is:

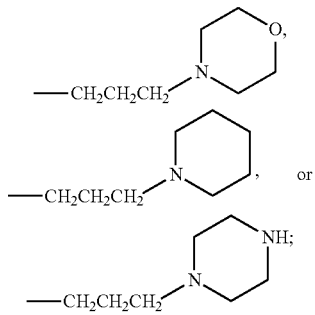

and
R² is —CH₃ or —CH₂CH₃; or
a pharmaceutically acceptable salt thereof.

In an embodiment the compound of formula I is of formula IA in which R¹ is

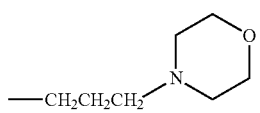

and R² is OCH₃, or a pharmaceutically acceptable salt thereof. In certain embodiments, the compound of formula IA is a mono-HCl salt, a di-HCl salt, or a mixture thereof.

The present invention includes a method of inhibiting a receptor tyrosine kinase in a subject in need thereof. The present invention includes a method of inhibiting the growth of a tumor cell in a subject in need thereof. The present invention includes a method of treating pancreatic cancer in a subject in need of treatment for pancreatic cancer. The present invention includes a method of treating HER2 positive breast cancer in a subject in need of treatment for HER2 positive breast cancer. The present invention includes a method of treating drug resistant non-small cell lung cancer in a subject in need of treatment for drug resistant non-small cell lung cancer. Each of these methods can include administering to the subject an effective amount of a compound of formula (I), which compound is described above, or a pharmaceutically acceptable salt thereof. The method can employ a compound of formula (I) in which R¹ and R², are as described in embodiments above. The method can employ a compound of formula (IA), which compound is described above, or a pharmaceutically acceptable salt thereof.

The present invention includes a pharmaceutical composition including a pharmaceutically acceptable carrier and a compound of formula (I). The pharmaceutical composition can include a compound of formula (I), which compound is described above, or a pharmaceutically acceptable salt thereof. The pharmaceutical composition can include a compound of formula (I) in which R¹ and R², are as described in embodiments above. The pharmaceutical composition can include a compound of formula (IA), which compound is described above, or a pharmaceutically acceptable salt thereof.

The present invention includes a process for preparing a compound of formula (I). The process can include reacting a quinazoline of formula II:

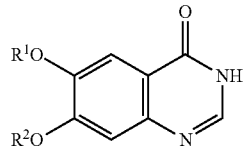

with phosphoryl chloride or oxalyl chloride to produce a chloro quinazoline of formula (III):

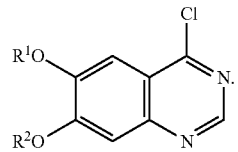

The process can also include condensing the 4-chloroquinazolne of formula III with 3-ethylnyl aniline to produce the quinazoline derivative of formula (I). In this process, R¹ and R² are as described above. This process can produce a compound of formula (IA).

BRIEF DESCRIPTION OF THE FIGURES

FIG. 1 is an image of relevant portions of a Western blot of A549 cells treated with erlotinib HCl and NRC 2694 (the compound of formula IA). Both compounds produced a dose dependent decrease in EGFR levels.

FIG. 2 is a series of images that show the results obtained from the Matrigel invasion assay of H1299 cells treated with Erlotinib and NRC 2694 (the compound of formula IA). Both compounds produced a dose dependent decrease in invasion.

FIG. 3 is a series of images that show the decrease in tumor size induced by oral and ip administration of Erlotinib HCl and NRC 2694 (the compound of formula IA) in nude mice implanted with A549 human lung tumors.

FIG. 4 is a series of images that show lungs harvested from nude mice that had been implanted with luciferase expressing A549 cells and treated with various concentrations of erlotinib HCl and NRC-2694 by oral and ip routes. Complete regression of tumors was observed in the treatment group with NRC-2694 (the compound of formula IA), whereas tumors were still present in the group treated with erlotinib.

FIG. 5 is a series of images that show representative stained sections of tumor bearing lungs removed from nude mice after treatment with Erlotinib HCl and NRC 2694 (the compound of formula IA).

FIG. 6 is a series of images that show nude mice that had been implanted with luciferase expressing A549 cells and treated with various concentrations of erlotinib HCl by oral and ip routes.

FIG. 7 is a series of images that show nude mice that had been implanted with luciferase expressing A549 cells and treated with various concentrations of NRC 2694 (the compound of formula IA) by oral and ip routes.

FIG. 8 is an image of relevant portions of a Western blot of A549 cells treated with erlotinib HCl and NRC 2694 (the compound of formula IA) and showing dose dependent decrease in levels of Erb1, ErbB2, ErbB3 and ErbB4 after treatment with NRC 2694 (the compound of formula IA).

FIG. 9 is a graph illustrating the results of experiments that compared the compound of formula IA to erlotinib and gemcitabine in causing tumor regression.

FIG. 10 shows results of immunohistochemical analysis of pancreatic sections (anti-angiogenic activity) for animals treated with the compound of formula IA, erlotinib and gemcitabine in causing tumor regression.

FIG. 11 is a graph illustrating the results of experiments that compared the compound of formula IA to lapatinib in causing tumor regression.

FIG. 12 is a graph illustrating the results of experiments that established regression of drug resistant tumors caused by the compound of formula IA.

DETAILED DESCRIPTION OF THE INVENTION

Definitions

As used herein, the term "therapeutically effective dose" refers to a dose of the present compound of formula I (e.g., formula IA) that provides an amount of present compound in and around a tumor cell effective to achieve a desired biological activity of the present compound, e.g., reducing the rate of or stopping the growth of the tumor cell or killing the tumor cell. Desired biological activities include inhibiting EGFR tyrosine kinase of the tumor cell. Inhibiting the growth of a cell can include, for example, reducing the number of divisions the cell undergoes (e.g., to zero), killing the cell, reducing the population of a plurality of such cells, or the like.

As used herein, the term "effective amount" of the present compound of formula I (e.g., formula IA) is an amount sufficient to prevent, treat, reduce and/or ameliorate the symptoms and/or underlying causes of cancer or growth of a tumor cell. In some instances, an "effective amount" is sufficient to eliminate the symptoms of cancer or the growth of the tumor cell and, perhaps, overcome the cancer (e.g., put the cancer into remission) or the growth of the tumor cell. In the context of the present invention, the terms "treat" and "therapy" and the like refer to alleviate, slow the progression, prophylaxis, attenuation or cure of existing disease (e.g., cancer or growth of a tumor cell). Prevent, as used herein, refers to putting off, delaying, slowing, inhibiting, or otherwise stopping, reducing or ameliorating the onset of such diseases or disorders (e.g., cancer or growth of a tumor cell). It is preferred that a large enough quantity of the agent be dosed in non-toxic levels in order to provide an effective level of activity within the subject against the disease. The method of the present invention may be used with any mammal. Suitable mammals include, but are not limited to rats, cats, dogs, horses, cows, sheep, pigs, and, preferably, humans.

The Present Compounds

The present invention relates to a compound of formula (I):

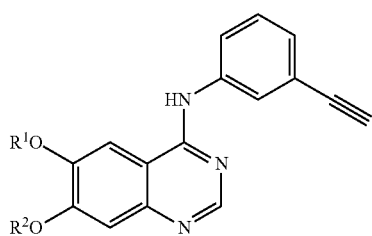

Formula I in which:

$R^1$ is:

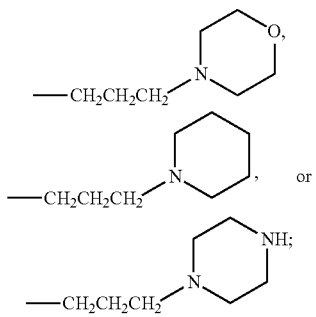

and $R^2$ is —$CH_3$ or —$CH_2CH_3$; or a pharmaceutically acceptable salt of the compound of formula (I). Suitable pharmaceutically acceptable salts include a monohydrochloride, a dihydrochloride, or a mixture thereof. Such a compound can be referred to as a quinazoline derivative.

In an embodiment of the present compound, $R^1$ is:

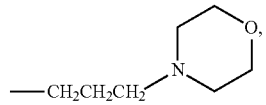

and $R^2$ is —$CH_3$. This embodiment can also be a pharmaceutically acceptable salt of the compound of formula (I). In an embodiment, the pharmaceutically acceptable salt is a monohydrochloride salt. In an embodiment, the pharmaceutically acceptable salt is a dihydrochloride salt. In an embodiment, the pharmaceutically acceptable salt is mixture of monohydrochloride and dihydrochloride salts. The compound of this embodiment can be referred to as the compound of formula (IA):

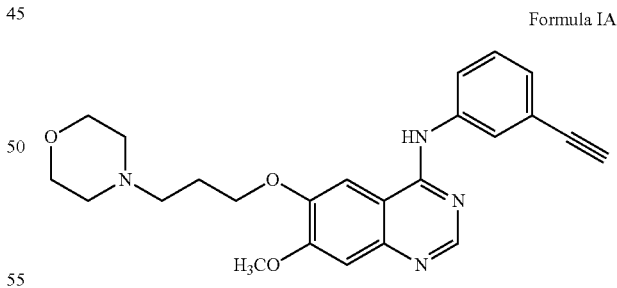

Formula IA

The Present Methods

The present invention includes a variety of methods employing the compound of the present invention. In an embodiment, the present method includes a method of inhibiting a receptor tyrosine kinase in a subject in need thereof. This embodiment of the method can include administering to the subject an effective amount of a quinazoline derivative of formula (I), which compound is described above, or a pharmaceutically acceptable salt thereof. This embodiment of the method can employ a compound of formula (I) in which $R^1$ is:

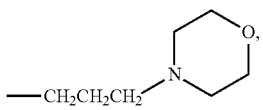

and $R^2$ is —$CH_3$. This embodiment of the method can employ a compound of formula (IA), which compound is described above, or a pharmaceutically acceptable salt thereof. The pharmaceutically acceptable salt employed in the method can be a monohydrochloride, a dihydrochloride, or a mixture thereof. The tyrosine kinase can be an EGF receptor tyrosine kinase. The tyrosine kinase can be an Erb-2 tyrosine kinase, an Erb-3 tyrosine kinase, an Erb-4 tyrosine kinase, or a plurality (or mixture) thereof. The tyrosine kinase can be an Erb-2 tyrosine kinase. The tyrosine kinase can be an Erb-3 tyrosine kinase. The tyrosine kinase can be an Erb-4 tyrosine kinase. The tyrosine kinase can be a VEGF receptor tyrosine kinase. The tyrosine kinase can be a plurality or mixture of these tyrosine kinases.

In an embodiment, the present method includes a method of inhibiting the growth of a tumor cell in a subject in need thereof. This embodiment of the method can include administering to the subject an effective amount of a quinazoline derivative of formula (I), which compound is described above, or a pharmaceutically acceptable salt thereof. This embodiment of the method can employ a compound of formula (I) in which $R^1$ and $R^2$, are as described in embodiments above. This embodiment of the method can employ a compound of formula (IA), which compound is described above, or a pharmaceutically acceptable salt thereof. In an embodiment, the tumor cell expresses an EGF receptor tyrosine kinase. In an embodiment, the tumor cell (or population of tumor cells) expresses an Erb-2 tyrosine kinase, an Erb-3 tyrosine kinase, an Erb-4 tyrosine kinase, or a plurality (or mixture) thereof. In an embodiment, the tumor cell expresses an Erb-2 tyrosine kinase. In an embodiment, the tumor cell expresses an Erb-3 tyrosine kinase. In an embodiment, the tumor cell expresses an Erb-4 tyrosine kinase. In an embodiment, the tumor cell expresses a VEGF receptor tyrosine kinase. In an embodiment, the tumor cells expressing one or more express a plurality or mixture of these tyrosine kinases. In an embodiment, the tumor cell is a pancreatic cancer cell. In an embodiment, the tumor cell is a HER2 positive breast cancer cell. In an embodiment, the tumor cell is a drug resistant non-small cell lung cancer cell. In an embodiment, the drug is erlotinib, gefitinib, or a plurality thereof.

In an embodiment, the present method includes a method of treating pancreatic cancer in a subject in need of treatment for pancreatic cancer. This embodiment of the method can include administering to the subject an effective amount of a quinazoline derivative of formula (I), which compound is described above, or a pharmaceutically acceptable salt thereof. This embodiment of the method can employ a compound of formula (I) in which $R^1$ and $R^2$, are as described in embodiments above. This embodiment of the method can employ a compound of formula (IA), which compound is described above, or a pharmaceutically acceptable salt thereof.

In an embodiment, the present method includes a method of treating HER2 positive breast cancer in a subject in need of treatment for HER2 positive breast cancer. This embodiment of the method can include administering to the subject an effective amount of a quinazoline derivative of formula (I), which compound is described above, or a pharmaceutically acceptable salt thereof. This embodiment of the method can employ a compound of formula (I) in which $R^1$ and $R^2$, are as described in embodiments above. This embodiment of the method can employ a compound of formula (IA), which compound is described above, or a pharmaceutically acceptable salt thereof.

In an embodiment, the present method includes a method of treating drug resistant non-small cell lung cancer in a subject in need of treatment for drug resistant non-small cell lung cancer. In an embodiment, the drug is erlotinib, gefitinib, or a plurality thereof. These embodiments of the method can include administering to the subject an effective amount of a quinazoline derivative of formula (I), which compound is described above, or a pharmaceutically acceptable salt thereof. These embodiments of the method can employ a compound of formula (I) in which $R^1$ and $R^2$, are as described in embodiments above. This embodiment of the method can employ a compound of formula (IA), which compound is described above, or a pharmaceutically acceptable salt thereof.

Unexpected Advantages of the Compounds of the Present Invention

Compounds of the present invention exhibit unexpected advantages in methods of the present invention. For example, compounds of the present invention (e.g., a compound of formula (IA)) has exhibited unexpectedly superior anti-cancer and anti-proliferative effects compared to known compounds such as erlotinib, gefitinib, and lapatinib.

The compounds of the present invention (e.g., a compound of formula (IA)) exhibited unexpectedly increased potency compared to erlotinib in each of several assays for anticancer and antiproliferative activity. In the MTT proliferation assay, compounds of the present invention exhibited an $IC_{50}$ of 40-90 ng/ml (100-200 nm) whereas erlotinib HCl showed a value of 836 ng/ml (1945 nm). The same trend was shown by western blot analysis and the Matrigel invasion assay.

The compounds of the present invention (e.g., a compound of formula (IA)) unexpectedly caused complete tumor regression in an animal model that is indicative of efficacy of such compounds. Complete tumor regression was observed after oral administration of compounds of the present invention to nude mice implanted with A549 human lung tumor cells at 10 mg/kg dose. In the control, even at 100 mg/kg dose, erlotinib HCl could not induce complete tumor regression. Visual examination of lung tissue of the mice implanted with A549 and luciferase expression experiments confirmed the same result. Further, the compound of formula (IA) provided curative effect of 100% compared to only 50-60% in the case of erlotinib HCl. The compound of formula IA is unexpectedly more potent and more curative than erlotinib.

The compounds of the present invention (e.g., a compound of formula (IA)) exhibited increased potency in vivo. The compound of formula (IA) had a value ($ED_{50}$) of 6.3 mg/kg. In comparison, the value obtained with erlotinib HCl was 22 mg/kg. The compound of formula IA was unexpectedly more potent than erlotinib.

The compounds of the present invention (e.g., a compound of formula (IA)) down regulated expression levels of ErbB2, ErbB3, ErbB4 and VEGFR receptors. Erlotinib does not down regulate expression of these receptors.

The compounds of the present invention (e.g., a compound of formula (IA)) exhibited activity against numerous kinases in in vitro assays. The compound of formula (IA) was evaluated for inhibition of 80 kinases in an in vitro kinase profiling study and significantly inhibited 15 of them.

The compound of formula (IA) was evaluated in an in vivo model of pancreatic cancer and found to be unexpectedly superior to erlotinib alone or in combination with gemcitabine. The compound of formula (IA) caused regression of subcutaneous pancreatic tumors in nude mice. The tumor regression observed was superior to that caused by the existing drugs erlotinib and gemcitabine.

The compound of formula (IA) was evaluated in an in vivo model of HER2 positive breast cancer. The tumor regression observed with the compound of formula (IA) in SCID mouse xenograft models of HER2 positive breast cancer was superior to that of Lapatinib, an approved drug of choice for treatment of HER2 positive breast cancer.

The compound of formula (IA) was evaluated in an in vivo model of drug (e.g., erlotinib or Gefitinib) resistant non-small cell lung cancer. The compound of formula (IA) showed significant anticancer activity in animals implanted with erlotinib/gefitinib resistant H1975 cells. Tumor regression was observed after withdrawal of treatment with the compound of formula (IA).

The compounds of the present invention (e.g., a compound of formula (IA)) exhibited an unexpectedly advantageous safety profile. The compound of formula (IA) exhibited a Maximum Tolerated Dose (MTD) of 2000 mg/kg as against 500 mg/kg for erlotinib HCl. The wide therapeutic window offered by NRC-2694 (the compound of formula IA) was demonstrated by its $LD_0$ value of 2000 mg/kg as against 500 mg/kg for erlotinib HCl. The $LD_{50}$ value could not be pinpointed for NRC-2694 (the compound of formula IA), whereas a value of 805 mg/kg was determined for erlotinib HCl.

Embodiments of the Present Methods

A compound of the present invention can be employed to inhibit a receptor tyrosine kinase. In certain embodiments, a compound of the present invention can inhibit a tyrosine kinase of an epidermal growth factor (EGF) receptor, an Erb-2 tyrosine kinase, an Erb-3 tyrosine kinase, an Erb-4 tyrosine kinase, a VEGF receptor tyrosine kinase, or a plurality thereof. In certain embodiments, the tyrosine kinase can be an isolated tyrosine kinase, a tyrosine kinase on an isolated cell, or a tyrosine kinase in an organism or subject.

In an embodiment, a compound of the present invention can be employed to inhibit the growth of a cell including a tyrosine kinase. For example, a compound of the present invention can inhibit the growth of a tumor cell or malignant cell that expresses a tyrosine kinase, such as an epidermal growth factor (EGF) receptor tyrosine kinase, an Erb-2 tyrosine kinase, an Erb-3 tyrosine kinase, an Erb-4 tyrosine kinase, or a VEGF receptor tyrosine kinase. Such a tumor cell or malignant cell can over express the receptor tyrosine kinase. In certain embodiments, the tumor or malignant cell is a lung cancer cell, a pancreatic cancer cell, or a breast cancer cell. In an embodiment, the cancer cell is a lung cancer cell. In an embodiment, the lung cancer cell is a non-small cell lung cancer cell. In an embodiment, the non-small cell lung cancer cell is a drug resistant (e.g., erlotinib or gefitinib resistant) non-small cell lung cancer cell. In an embodiment, the cancer cell is a pancreatic cancer cell. In an embodiment, the cancer cell is a breast cancer cell. In an embodiment, the breast cancer cell is a cell that expresses HER2. In certain embodiments, the present compound can inhibit the growth of the tumor cell or malignant cell in vitro, ex vivo, or in vivo.

In an embodiment, the method can include contacting the tyrosine kinase with a compound of the present invention. In an embodiment, the method can include contacting a cell expressing the tyrosine kinase with a compound of the present invention. In an embodiment, the method can include contacting a tumor containing a cell expressing the tyrosine kinase with the compound of the present invention. In certain embodiments, the present method can include contacting in vitro, ex vivo, or in vivo.

In an embodiment, the method can include contacting a tumor cell or malignant cell that expresses a tyrosine kinase, such as an epidermal growth factor (EGF) receptor tyrosine kinase, an Erb-2 tyrosine kinase, an Erb-3 tyrosine kinase, an Erb-4 tyrosine kinase, or a VEGF receptor tyrosine kinase with a compound of the present invention. In certain embodiments, the method can include contacting a lung cancer cell, a pancreatic cancer cell, or a breast cancer cell with a compound of the present invention. In an embodiment, the method can include contacting a lung cancer cell with a compound of the present invention. In an embodiment, the method can include contacting a non-small cell lung cancer cell with a compound of the present invention. In an embodiment, the method can include contacting a drug resistant (e.g., erlotinib or gefitinib resistant) non-small cell lung cancer cell with a compound of the present invention. In an embodiment, the method can include contacting a pancreatic cancer cell with a compound of the present invention. In an embodiment, the method can include contacting a breast cancer cell with a compound of the present invention. In an embodiment, the method can include contacting a breast cancer cell that expresses HER2 with a compound of the present invention. In certain embodiments, the present method can include contacting in vitro, ex vivo, or in vivo.

In an embodiment, the method can include contacting a tumor that expresses a tyrosine kinase, such as an epidermal growth factor (EGF) receptor tyrosine kinase, an Erb-2 tyrosine kinase, an Erb-3 tyrosine kinase, an Erb-4 tyrosine kinase, or a VEGF receptor tyrosine kinase with a compound of the present invention. In certain embodiments, the method can include contacting a lung cancer tumor, a pancreatic cancer tumor, or a breast cancer tumor with a compound of the present invention. In an embodiment, the method can include contacting a lung cancer tumor with a compound of the present invention. In an embodiment, the method can include contacting a non-small cell lung cancer tumor with a compound of the present invention. In an embodiment, the method can include contacting a drug resistant (e.g., erlotinib or gefitinib resistant) non-small cell lung cancer tumor with a compound of the present invention. In an embodiment, the method can include contacting a pancreatic cancer tumor with a compound of the present invention. In an embodiment, the method can include contacting a breast cancer tumor with a compound of the present invention. In an embodiment, the method can include contacting a breast cancer tumor that expresses HER2 with a compound of the present invention. In certain embodiments, the present method can include contacting in vitro, ex vivo, or in vivo.

In an embodiment, the method can include administering the compound of the present invention to a subject (e.g., a mammal or a warm blooded animal) having a tumor containing a cell expressing the tyrosine kinase. In an embodiment, the method can include administering the compound of the present invention to a subject (e.g., a mammal or a warm blooded animal) having a tumor cell or malignant cell that expresses a tyrosine kinase, such as an epidermal growth factor (EGF) receptor tyrosine kinase, an Erb-2 tyrosine kinase, an Erb-3 tyrosine kinase, an Erb-4 tyrosine kinase, or a VEGF receptor tyrosine kinase. In certain embodiments, the method can include administering the compound of the present invention to a subject (e.g., a mammal or a warm blooded animal) having lung cancer, pancreatic cancer, or breast cancer. In an embodiment, the method can include administering the compound of the present invention to a subject (e.g., a mammal or a warm blooded animal) having lung cancer. In an embodiment, the method can include administering the compound of the present invention to a subject (e.g., a mammal or a warm blooded animal) having non-small cell lung cancer. In an embodiment, the method can include administering the compound of the present invention to a subject (e.g., a mammal or a warm blooded animal) having drug resistant (e.g., erlotinib or gefitinib resistant) non-small cell lung cancer cell. In an embodiment, the method can include administering the compound of the present invention to a subject (e.g., a mammal or a warm blooded animal) having pancreatic cancer. In an embodiment, the method can include administering the compound of the present invention to a subject (e.g., a mammal or a warm blooded animal) having breast cancer. In an embodiment, the method can include administering the compound of the present invention to a subject (e.g., a mammal or a warm blooded animal) having breast cancer that expresses HER2. In an embodiment, the subject is a human.

The methods have been described with reference to "a compound of the present invention." In the description of the methods of the invention, the phrase "a compound of the present invention" can be replaced by the phrase "a pharmaceutically acceptable salt of a compound of the present invention", the phrase "a pharmaceutical composition including a compound of the present invention" or the phrase "a pharmaceutical composition including a pharmaceutically acceptable salt of a compound of the present invention" to describe additional embodiments of the present methods.

The compound of the present invention can be administered at a dose sufficient to provide a therapeutically effective level at a tumor cell in the subject. It is recognized that the total amount of compound of the present invention administered as a unit dose to a subject will depend upon the type of pharmaceutical composition being administered. It should be apparent to a person skilled in the art that variations may be acceptable with respect to the therapeutically effective dose and frequency of the administration of compound of the present invention in this embodiment of the invention. The amount of the compound of the present invention administered will be inversely correlated with the frequency of administration. Hence, an increase in the concentration of compound of the present invention in a single administered dose, or an increase in the mean residence time in the case of a sustained release form of compound of the present invention, generally will be coupled with a decrease in the frequency of administration.

The actual dose of the compound of the present invention will depend on a variety of factors that may be specific to the subject undergoing dosing. These factors should be taken into consideration when determining the therapeutically effective dose of compound of the present invention and frequency of its administration. For example, the effective dose can depend on the species, age, weight, or general health of the subject; the severity of the cancer or tumor growth; the size and location of the tumor in which an effective amount of agent must be achieved; the frequency and duration of dosing; the type of formulation administered; and the like. Generally, a higher dosage is preferred if the disease or disorder is more severe.

Methods of Making the Present Compounds

The present invention includes methods or processes for making the compounds of the invention. Scheme 1 illustrates an embodiment of a process for making compounds of the present invention.

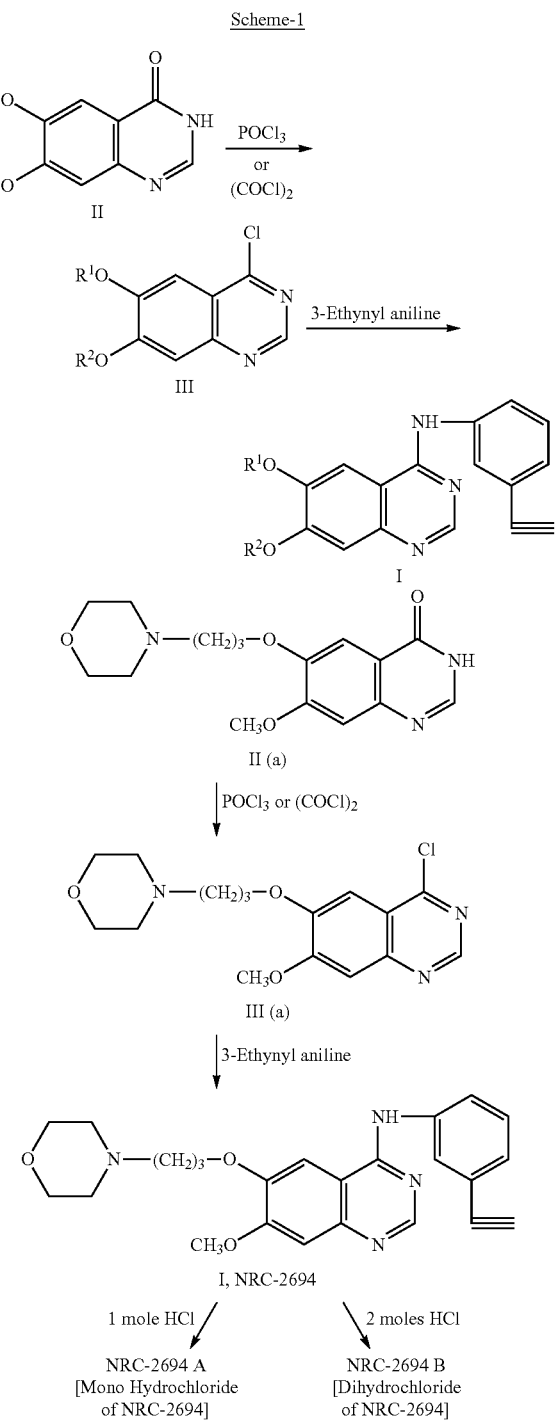

In an embodiment, the present method includes a method for preparing a quinazoline derivative of formula (I)

Formula I

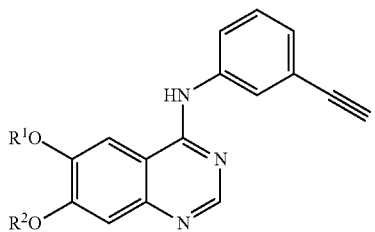

in which:
R¹ is:

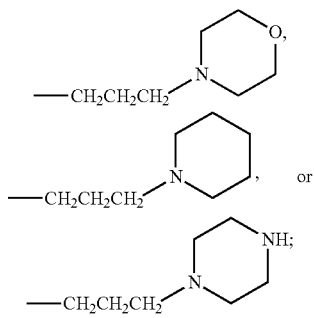

and R² is —CH₃ or —CH₂CH₃; or a pharmaceutically acceptable salt thereof. This embodiment of the process includes reacting a quinazoline of formula II:

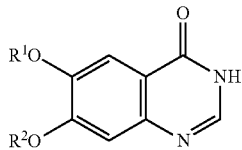

with phosphoryl chloride or oxalyl chloride to produce a chloro quinazoline of formula (III):

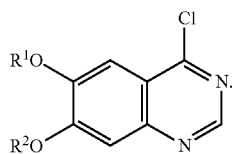

This embodiment also includes condensing the 4-chloroquinazolne of formula III with 3-ethylnyl aniline to produce the quinazoline derivative of formula (I). In an embodiment of this process, R¹ is:

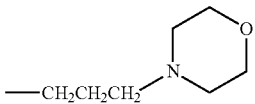

and R² is —CH₃.

In an embodiment, the present method includes a method for preparing a quinazoline derivative of formula (IA):

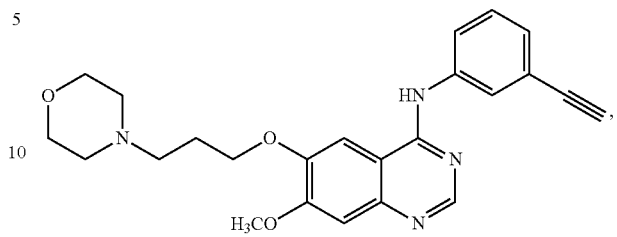

or a pharmaceutically acceptable salt thereof. This embodiment of the process includes reacting the quinazoline of formula (IIa):

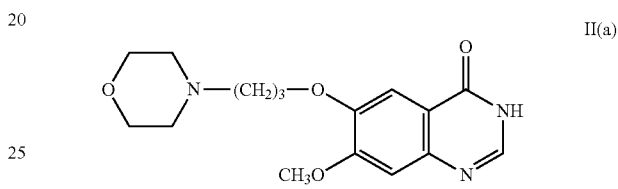

with phosphoryl chloride or oxalyl chloride to produce the corresponding 4-chloro quinazoline of formula (IIIa):

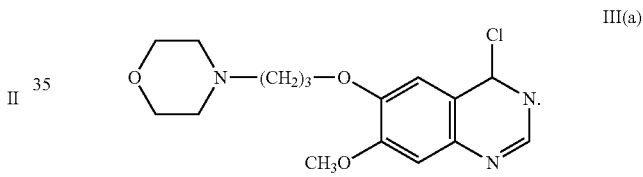

This embodiment also includes condensing the 4-chloroquinazolne of formula III(a) with 3-ethylnyl aniline to produce the quinazoline derivative of formula (IA).

Pharmaceutical Compositions

The present composition can include a pharmaceutically acceptable carrier mixed with the compound of the present invention and other components in the pharmaceutical composition. As used herein, the term "pharmaceutically acceptable carrier" refers to a carrier that is conventionally used to facilitate the storage, administration, and/or the healing effect of the an anticancer or antiproliferative agent. A carrier may also reduce any undesirable side effects of the agent. A suitable carrier should be stable, i.e., incapable of reacting with other ingredients in the formulation. It should not produce significant local or systemic adverse effect in recipients at the dosages and concentrations employed for treatment. Such carriers are generally known in the art.

Suitable ingredients for the present pharmaceutical composition include albumin, gelatin, collagen, polysaccharide, monosaccharide, polyvinylpyrrolidone, polylactic acid, polyglycolic acid, polymeric amino acids, fixed oils, ethyl oleate, liposome, glucose, sucrose, lactose, mannose, dextrose, dextran, cellulose, mannitol, sorbitol, polyethylene glycol (PEG), starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, microcrystalline cellulose, mannitol, carboxymethyl cellulose, hydroxypropyl methylcellulose, hyaluronic acid, alginate, chondroitin sulfate, maltodextrin, dextran sulfate, and the like. The compositions can be subjected to conventional pharmaceutical expedients, such as sterilization, and can contain conventional pharmaceutical additives, such as preservatives, stabilizing agents, wetting, or emulsifying agents, salts for adjusting osmotic pressure, buffers, and the like.

The present invention includes a pharmaceutical composition including a pharmaceutically acceptable carrier and a quinazoline derivative of formula (I), which compound is described above, or a pharmaceutically acceptable salt thereof. The pharmaceutical composition can include a compound of formula (I) in which $R^1$ and $R^2$ are as described in embodiments above. The pharmaceutical composition can include a compound of formula (IA), which compound is described above, or a pharmaceutically acceptable salt thereof.

In an embodiment, the pharmaceutical composition can include about 20 wt-% compound of formula I (e.g., IA), about 60 to about 65 wt-% lactose, about 5 to about 10 wt-% microcrystalline cellulose, about 1 to about 5 wt-% anionic surfactant, about 2 to about 10 wt-% sodium starch glycolite, about 1 to about 5 wt-% polyvinylpyrrolidone, about 2 to about 10 wt-% hydroxypropyl cellulose, and about 0.1 to about 1 wt-% magnesium stearate. In an embodiment, the pharmaceutical composition is in the form of a tablet comprising 50 mg of the compound of formula I.

In an embodiment, the pharmaceutical composition can include:

| Tablet | mg/tablet |
| --- | --- |
| Compound NRC-2694 (the compound of formula IA) or a salt thereof | 50 |
| Lactose anhydrous (USP) | 156 |
| Microcrystalline cellulose (Avicel pH102) | 15 |
| Sodium lauryl sulfate | 5 |
| Sodium starch glycolite | 10 |
| Povidone K-30 | 3 |
| Hydroxy propyl cellulose (LH-11) | 10 |
| Magnesium stearate | 1 |

The agent of the present invention can also be formulated in a sustained-release form to prolong the presence of the pharmaceutically active agent in the treated mammal, generally for longer than one day. Many methods of preparation of a sustained-release formulation are known and are disclosed in Remington's Pharmaceutical Sciences (18th ed.; Mack Publishing Company, Eaton, Pa., 1990). For example, the agent can be entrapped in semipermeable matrices of solid hydrophobic polymers. The matrices can be shaped into films or microcapsules. Examples of such matrices include, but are not limited to, polyesters, copolymers of L-glutamic acid and gamma ethyl-L-glutamate, polylactides, polylactate polyglycolate (PLGA) such as polylactide-co-glycolide, hydrogels, non-degradable ethylene-vinyl acetate (e.g. ethylene vinyl acetate disks and poly(ethylene-co-vinyl acetate)), degradable lactic acid-glycolic acid copolyers such as the Lupron Depot™, poly-D-(−)-3-hydroxybutyric acid, hyaluronic acid gels, alginic acid suspensions, and the like.

Articles and Methods of Manufacture

The present invention also includes an article of manufacture providing an agent for administration to a subject having a tumor or to a tumor cell. The article of manufacture can include a container which contains a composition (e.g., tablet) suitable for the present method. The article of manufacture further includes instructions in the form of a label on the container and/or in the form of an insert included in a box in which the container is packaged, for the carrying out the method of the invention. The instructions can also be printed on the box in which the container is packaged. The instructions contain information such as sufficient dosage and administration information so as to allow the subject or a worker in the field to administer the present compound or pharmaceutical composition. It is anticipated that a worker in the field encompasses any doctor, nurse, technician, spouse, or other caregiver who might administer the agent. The agent can also be self-administered by the subject.

According to the invention, the present compound of formula I (e.g., compound of formula IA) can be used for manufacturing an composition or medicament including the compound and suitable for oral or parenteral administration. The invention also relates to methods for manufacturing a composition or medicament including a compound of formula I (e.g., compound of formula IA) suitable for oral or parenteral administration. For example, a tablet can be manufactured in several ways, using conventional techniques. A liquid composition can be manufactured by dissolving an agent in a suitable solvent, such as water, at an appropriate pH, including buffers or other excipients, for example, to form a solution.

The present invention may be better understood with reference to the following examples. These examples are intended to be representative of specific embodiments of the invention, and are not intended as limiting the scope of the invention.

EXAMPLES

Example 1

Preparation of N-(3-ethylnylphenyl)-7-methoxy-6-[3-(4-morpholinyl)propoxy]-4-quinazolinamine (IA)

i) Preparation of 4-Chloro-6-[3-(4-morpholinyl) propoxy-4-quinazoline (IIIa)

Into a clean and dried 5-Liter four necked round bottomed flask equipped with a mechanical stirrer, reflux-condenser, pressure equalizing addition funnel, and thermometer socket were charged chloroform (3000 ml), dimethyl formamide (30 ml) followed by 7-methoxy-6-(3-morpholino propoxy)-3,4-dihydro-quinazolin-4-one (IIa) (150 g), obtained according to the process given in Example-1 of PCT international application published as WO.2005/070909A$_1$. Oxalyl Chloride (120 g) was slowly added and the reaction mass was heated to reflux temperature and maintained at reflux temperature for about 5 hours. Reaction was found to be completed by HPLC test. The solvent chloroform and excess oxalyl chloride were distilled off by applying mild vacuum. The reaction mass was cooled to about 40° C. and added chloroform (300 ml) and again distilled out the solvent by applying mild vacuum. The reaction mixture was cooled to room temperature and acetonitrile (3000 ml) was added and stirred for 10-15 minutes and kept under nitrogen atmosphere to proceed to the next step.

ii) Preparation of N-(3-ethylnylphenyl)-7-methoxy-6-[3-(4-morpholinyl)propoxy]-4-quinazolinamine (IA)

Into a 5-Liter four necked round bottomed flask equipped with a mechanical stirrer, reflux-condenser and thermometer socket containing the chloro compound in acetonitrile from the above step-(i); 3-ethynyl aniline (69 g) was added slowly in about 10-15 minutes and the reaction mass was heated to reflux temperature and maintained at reflux temperature for about 4 hrs. The reaction was found to be completed by HPLC test. Then the reaction mass was cooled to 25-35° C. and filtered, washed the cake with acetonitrile (500 ml) and dried the cake.

The above dried crude compound was taken into a another 5 liter round bottomed flask and charged water (2500 ml) and slowly raised the temperature to 60-65° C. and was adjusted the pH of the reaction mass to 10-12 with dilute sodium hydroxide solution. The solid product separated was filtered and washed with water and dried at 70-75° C. to get 173.0 g of N-(3-ethynylphenyl)-6-(3-morphiline propoxy)-7-methoxy-4-quinazolamine as a off-white solid.

iii) Recrystallisation of Preparation of N-(3-ethylnylphenyl)-7-methoxy-6-[3-(4-morpholinyl)propoxy]-4-quinazolinamine from Toluene Into a 5-Liter four necked round bottomed flask equipped with a mechanical stirrer, reflux-condenser and thermometer socket were charged toluene (3750 ml), followed by N-(3-ethynylphenyl)-6-(3-morpholino propoxy)-7-methoxy-4-quinazolinamine (50 g) obtained by the process described in the above given example-(1). The reaction mixture was heated to 90-95° C., so that the solid completely dissolved. Then carbon treatment was given and filtered. The filtrate was cooled to 25-35° C., maintained for about 1 hour and filtered and dried the material to get 40.15 g of N-(3-ethylnylphenyl)-7-methoxy-6-[3-(4-morpholinyl)propoxy]-4-quinazolinamine as a white crystalline solid.

mp: 185-187° C.
Purity: 99.72% (HPLC)
IR (KBr) (cm$^{-1}$): 3280.9, 2954.6, 2810.3, 1620.1, 1604.2, 1572.1, 1527.7, 1505.2, 1484, 1430.5, 1388.2, 1247.5, 1211.2, 1140.3, 1110.4, 1010.3, 953.4, 859.6, 784.2 Cm$^{-1}$
$^1$HNMR (300 MH$_z$; DMSO-d$_6$): 9.57 (s, 1H); 8.48 (s, 1H); 7.99 (s, 1H); 7.86 to 7.92 (d, 2H); 7.34 to 7.44 (t, 1H) 7.18 to 7.21 (s, 2H); 4.15 to 4.21 (t, 4H); 3.92 (s, 3H) 3.5 to 3.6 (t, 4H); 2.4 to 2.52 (m, 5H); 1.95 to 2.01 (m, 2H).
Mass: 419.4 (M+1)

Example 2

Recrystallisation of N-(3-ethylnylphenyl)-7-methoxy-6-[3-(4-morpholinyl)propoxy]-4-quinazolinamine from acetonitrile Into a two liter three necked round bottomed flask equipped with a mechanical stirrer, reflux-condenser and thermometer socket were charged acetonitrile (1000 ml), followed by N-(3-ethylnylphenyl)-7-methoxy-6-[3-(4-morpholinyl)propoxy]-4-quinazolinamine (25 g) obtained from the process described in the above given Example-(1). The reaction mass was slowly heated to 65-70° C., so that the solid material completely dissolved and carbon treatment was given and filtered the reaction mass. The filtrate was transferred into another round-bottomed flask and slowly cooled to 10-15° C. and maintained for 30 minutes at that temperature. The mass was filtered and after washing the cake with chilled acetonitrile dried to get 20.50 g of N-(3-ethylnylphenyl)-7-methoxy-6-[3-(4-morpholinyl)propoxy]-4-quinazolinamine as a white crystalline solid.

mp: 186-187° C.;
Purity: 99.68% (HPLC)

Example 3

Recrystallisation of N-(3-ethylnylphenyl)-7-methoxy-6-[3-(4-morpholinyl)propoxy]-4-quinazolinamine from Ethyl acetate Into a three liter three necked round bottomed flask equipped with a mechanical stirrer, reflux-condenser and thermometer socket were charged ethyl acetate (2000 ml), followed by N-(3-ethylnylphenyl)-7-methoxy-6-[3-(4-morpholinyl)propoxy]-4-quinazolinamine (25 g) obtained from the process described in the above given Example-(1). The reaction mass was slowly heated to 65-70° C., so that the solid material completely dissolved and carbon treatment was given and filtered the reaction mass. The filtrate was transferred into another round-bottomed flask and slowly cooled to 10-15° C. and maintained for 30 minutes at that temperature. The crystalline mass was filtered and after washing the cake with chilled ethyl acetate dried to get 20.95 g of N-(3-ethynlphenyl)-6-(3-morpholino propoxy)-7-methoxy-4-quinazolinamine as a white crystalline solid.

mp: 185-187° C.
Purity: 99.7% (HPLC)

Example 4

Preparation of N-(3-ethylnylphenyl)-7-methoxy-6-[3-(4-morpholinyl)propoxy]-4-quinazolinamine mono hydrochloride (IA monohydrochloride)

Into a 500 ml three necked round bottomed flask equipped with a mechanical stirrer, reflux-condenser, thermometer socket etc. charged Isopropyl alcohol (250 ml), followed by N-(3-ethylnylphenyl)-7-methoxy-6-[3-(4-morpholinyl)propoxy]-4-quinazolinamine (5 g), obtained from the process given in Example-1. The temperature of the reaction mass was raised to 65-70° C. so that all the solid material dissolves and carbon treatment was given and filtered. The filtrate was cooled to about 55 to 60° C. and to this one mole equivalent of HCl-gas dissolved in isopropyl alcohol solution was added when the mono hydrochloride salt separated out. The reaction mass was maintained at reflux temperature for about 2 hrs and then cooled to room temperature and filtered and dried to get 5.1 g. of N-(3-ethynyl phenyl)-6-(3-morpholino propoxy)-7-methoxy-4-quinazolinamine mono hydrochloride as a white crystalline substance.

Purity: 99.8% (HPLC)
HCl content (chemical): 8.19% (Theoretical value: 8.01%)
IR (KBr) (cm$^{-1}$): 3407, 3305, 3259.5, 2934, 2619, 1625.9, 1593.8, 1579.9, 1530.8, 1512, 1476.9, 1392.2, 1356.8, 1282.1, 1242.1, 1207.9, 1141.3, 1100.8, 1076.1, 1042.1, 1026.5, 1011.5, 957.7, 941.5, 922.1, 857.3, 852, 838.1, 796, 782.4.

Example 5

Preparation of N-(3-ethylnylphenyl)-7-methoxy-6-[3-(4-morpholinyl)propoxy]-4-quinazolinamine di hydrochloride (IA dihydrochloride)

Into a 500 ml three necked round bottomed flask equipped with a mechanical stirrer, reflux-condenser and thermometer socket were charged Isopropyl alcohol (250 ml), followed by N-(3-ethylnylphenyl)-7-methoxy-6-[3-(4-morpholinyl)

propoxy]-4-quinazolinamine 5 g), obtained from the process given in Example-1. The temperature of the reaction mass was raised to 65-70° C. so that all the solid material dissolves. Carbon treatment was given and filtered. The filtrate was cooled to about 55 to 60° C. and to this two moles equivalent of HCl-gas dissolved in isopropyl alcohol solution was added when the dihydrochloride salt separated out. The reaction mass was maintained at reflux temperature for about 2 hrs and then cooled to room temperature and filtered and dried to get 5.5 g. of N-(3-ethylnylphenyl)-7-methoxy-6-[3-(4-morpholinyl)propoxy]-4-quinazolinamine di hydrochloride as a white crystalline substance.

Purity: 99.78% (HPLC)

HCl content (chemical): 14.9% (Theoretical value: 14.83%)

IR (KBr) (cm$^{-1}$): 3406.8, 3194.1, 2942.7, 2681.9, 2623.6, 1633.7, 1566.2, 1528.6, 1512.5, 1438.6, 1359.6, 1282.3, 1218.3, 1157.1, 1132.7, 1105.9, 1075.6, 1001.9, 942.1, 875.3, 816.1, 787.2

Example 6

Maximum Tolerated Dose (MTD) and Acute Toxicity Evaluation

The MTD Early citation study was done in male and female Swiss Albino mice (weighing 20-25 gm). The study was done as per OECD guidelines rule 420, the study was conducted between 9 am to 5 pm to avoid circadian cycle, the compounds Erlotinib and NRC-2694 (the compound of formula IA) were suspended with 2% gum acacia, the compounds were administered in doses of 5, 50, 300 and 2000 mg/Kg orally. The intermediate doses were administered depending upon mortality. The animals were observed for gross behavioral changes at every hour up to six hours after drug administration. The animals further observed up to 72 hours for mortality, if any. The animals that survived were euthanized and then autopsied for assessing the absorption of the test compound through the gastrointestinal tract (g.i.t.).

Acute toxicity of Erlotinib and NRC-2694 (the compound of formula IA) was carried out in male and female mice. The doses 500, 750, 1000 and 2000 mg/Kg were administered orally. Each group included 5 mice. The animals were observed for mortality for 14 days after compound administration. The survived animals were autopsied for asserting the absorption of compound through g.i.t. The $LD_{50}$ was determined according to the method described in Litchfield and Wilcoxon (J. Pharmacol. Exp. Ther. 1949, 96:99-113).

The results of the toxicity studies are tabulated in Tables 1 and 2. The Maximum Tolerated Dose (MTD) of erlotinib HCl was found to be 500 mg/Kg (po) whereas for NRC-2694 (the compound of formula IA), it is 2000 mg/Kg (po). Similarly, $LD_0$ was found to be 500 mg/Kg (po) for erlotinib HCl and 2000 mg/Kg (po) for NRC-2694 (the compound of formula IA). Thus, the unexpected and surprisingly low toxicity and safety profile of NRC-2694 (the compound of formula IA) over erlotinib HCl has been established.

TABLE 1

Maximum Tolerated Dose of Erlotinib HCl and NRC-2694 (IA) in Mice

| Compound | MTD mg/Kg (po) |
|---|---|
| Erlotinib HCl | 500 |
| NRC2694 | 2000 |

TABLE 2

Acute $LD_{50}$ in Mice (single dose, 7 days observation)

| Compound | $LD_0$ mg/Kg (po)* | $LD_{50}$ mg/Kg (po) |
|---|---|---|
| Erlotinib HCl | 500 | 805 |
| NRC2694 | 2000 | — |

*$LD_0$: No mortality was observed at end of 7 days.

Example 7

In Vitro and In Vivo Evaluation and Therapeutic Efficacy

Using the approved drug Erlotinib as a positive control, the biological activity of compounds of the present invention were tested.

MTT Proliferation Assay:

The MTT [3-(4,5-dimethylthiazol-2-yl)-2,5-diphenyltetrazolium bromide] assay, first described by Mosmann in 1983, is based on the ability of mitochondrial dehydrogenase enzyme from viable cells to cleave the tetrazolium rings of the pale yellow MTT and form dark blue formazan crystals largely impermeable to cell membranes, thus resulting in its accumulation within healthy cells. Solubilization of the cells by the addition of a detergent results in the liberation of the crystals, which are solubilized. The number of surviving cells is directly proportional to the level of the formazan product created. The color can then be quantified using a simple colorimetric assay. This assay was done using 0-1000 ng/ml concentrations of Erlotinib and the test compounds in A549 and H1299 cells. The protocol was based on ATCC and as per manufacturer's instructions (Catalog No.: 30-1010K)

From the MTT proliferation assay, it was determined that the inhibiting concentration ($IC_{50}$) of compounds of invention varied from 40-90 ng/ml (100-200 nm). In comparison, Erlotinib hydrochloride, used as a positive control, had a value as high as 836 ng/ml (1945 nm). Thus, the compounds of this invention are at least 10 times more potent than Erlotinib hydrochloride.

Western Blot Analysis (FIG. 1):

Test compound concentrations determined from the MTT proliferation assay were used to treat 1×10$^6$ H1299 or A549 cells in appropriate media for 72 hr, following which, cell lysates were extracted and fractionated on a 10% SDS PAGE gel under reducing conditions. The gels were blotted onto treated nylon membranes (Biorad) and immunoprobed for EGFR, P13K and AKT.

Significant change in EGFR expression was observed in a dose dependent manner. NRC-2694 (the compound of formula IA) at 80 ng (190 nm) concentrations caused comparable inhibition of EGFR expression with Erlotinib HCl at 800 ng (1860 nm) concentrations. NRC-2694 (the compound of formula IA) was effective at $\frac{1}{10}^{th}$ the dose of Erlotinib HCl.

Matrigel Invasion Assay (FIG. 2):

The in vitro invasiveness of H1299 and A549 cells in the presence of various concentrations of NRC compounds (as determined by MTT assay) was assessed using a modified Boyden chamber assay. Cells were treated with these compounds for 48 hr. 1×10$^6$ cells were suspended in 600'µl of serum-free medium supplemented with 0.2% BSA and placed in the upper compartment of the transwell chambers (Corning Costar Fisher Scientific cat #07-200-158, Pittsburgh Pa.) coated with matrigel (0.7 mg/ml). The lower compartment of the chamber was filled with 200'μl of serum medium and the cells were allowed to migrate for 24 hr. After incubation, the cells were fixed and stained with Hema-3 and quantified as previously described (Mohanam et al. 1993). The migrated cells were quantified as percent invasion. The compound NRC-2694 (the compound of formula IA) showed significant decrease in invasion in a dose dependent manner.

In Vivo Evaluation on Subcutaneous Lung Tumors in Nude Mice (FIG. 3):

Nude mice were implanted with $2 \times 10^6$ A549 cells in the right hind limb flank. Upon the observance of a tumour (>2 mm), mice were given oral or ip treatments of the test compounds including erlotinib HCl used as positive control. A dose of 100 mg/Kg of erlotinib HCl was identified as the base line dose.

Tumor sizes were measured and complete regression of tumors were observed in the mice treated with NRC-2694 (the compound of formula IA) at 10 mg/Kg dose. However tumors were still present in the control group treated similarly with erlotinib HCl even at 100 mg/Kg dose level. Thus, a ten fold superiority in efficacy of a compound of this invention (NRC-2694, IA) has been established.

Evaluation of Lung Tissue Harvested from Nude Mice after Treatment (Figure-4):

Lungs harvested from nude mice implanted with A549 luciferase expressing cells treated with various concentrations of erlotinib HCl and NRC-2694 (the compound of formula IA) by oral/ip routes were examined for residual tumors.

Complete regression of tumors was observed in the treatment group with NRC-2694 (the compound of formula IA), whereas tumors were still present in the group treated with erlotinib HCl, thus establishing the unexpected surprisingly superior efficacy of the compounds of this invention.

Examination by Visualization of Tumors in Lung Tissue (FIG. 5):

Nude mice were implanted by intrapulmonary injections of A549 cells. The mice were treated with oral/ip routes by erlotinib HCl and NRC 2694 (the compound of formula IA) at 2.5 and 20 mg/Kg doses. Thirty days after daily drug treatments, mice were sacrificed and lungs harvested. The lung tissues were fixed in 10% buffered formaldehyde, paraffin embedded and sectioned. The sections were H&E stained as per statutory protocols to visualize solid or diffuse tumors.

The group treated with NRC 2694 (the compound of formula IA) fared much better than those treated with erlotinib HCl at all dose levels thus establishing the superior efficacy of NRC 2694 (the compound of formula IA).

Nude Mice Implanted with A549 Luciferase Expressing Cells (FIGS. 6 &7):

Nude mice implanted with A549 luciferase expressing cells treated with various concentrations of erlotinib HCl and NRC-2694 (the compound of formula IA) by oral and ip routes were observed for tumors and the pictorial observations are given as FIGS. 6 and 7. It was observed that the group treated with NRC 2694 (the compound of formula IA) fared much better than the group treated with erlotinib HCl. No tumors were observed at the end of 42 days treatment with NRC 2694 (the compound of formula IA) whereas residual tumors were still present in the group treated with erlotinib HCl both by oral and ip routes.

Curative Effect from In Vivo Studies in Nude Mice:

The curative effect as a ratio of number of animals cured to the number of animals used in the study is tabulated and presented in Table 3.

TABLE 3

Curative effect of NRC-2694 (IA) and erlotinib HCl on lung cancer

| Drug | Concentration (mg/Kg) | Cure ratio |
|---|---|---|
| Erlotinib IP | 2.5 | 1/5 |
|  | 5 | 2/5 |
|  | 10 | 2/5 |
|  | 20 | 3/5 |
| Erlotinib oral | 2.5 | 2/5 |
|  | 5 | 0/5 |
|  | 10 | 1/5 |
|  | 20 | 2/5 |
| NRC 2694 IP | 2.5 | 1/5 |
|  | 5 | 1/5 |
|  | 10 | 3/5 |
|  | 20 | 5/5 (100%) |
| NRC 2694 oral | 2.5 | 1/5 |
|  | 5 | 2/5 |
|  | 10 | 3/5 |
|  | 20 | 3/5 |

It can be seen that the cure ratio is close to 100% in the case of NRC 2694 (the compound of formula IA) whereas the ratio is between 40-60% in the case of study group with erlotinib HCl.

Evaluation of $ED_{50}$:

$ED_{50}$ values were evaluated based on the lung section and tumor regression studies. A value of 6.3 mg/Kg was calculated for NRC 2694 (the compound of formula IA) whereas the value obtained for erlotinib HCl was 22 mg/Kg by oral route. Thus, the superior efficacy of the compound of the present invention is established.

Down Regulation of Receptors (HER1, HER2, HER3, HER4 and VEGFR) In Vitro (FIG. 8):

To determine the effect of NRC 2694 (the compound of formula IA) on the various other receptors of EGFR family (Erb/HER), human lung cancer cells A549 were treated with various concentrations of NRC 2694 (the compound of formula IA) along with erlotinib HCl for a side-by-side comparison. Levels of Erb-1, Erb-2, Erb-3, Erb-4 and VEGFR were determined by western blot analysis.

It was observed that NRC 2694 (the compound of formula IA) down regulated levels of Erb B2, Erb B3, Erb B4 and VEGFR levels effectively whereas no such indication was seen with erlotinib HCl. The additional inhibitory indication in the expression levels of the above mentioned receptors is clearly demonstrative of the unexpected and surprising property of a compound of this invention, NRC 2694 (the compound of formula IA).

Example 8

In Vitro Kinase Profiling of the Compound of Formula (IA)

NRC-2694 (the compound of formula IA) was found to possess activity various kinases from a panel of 80 kinases by the method of KinomeScan™ of Ambit Biosciences Corp, San Diego, Calif. The kinases were ABL1(F317L), ABL1(H396P), ABL1(Q252H), ABL1(Y253F), ADCK3, ADCK4, ALK, ARKS, AXL, BLK, BRSK2, CDK7, CIT, CLK4, CSNK1D, CSNK1E, DAPK1, DAPK3, DCAMKL3, DMPK, EGFR, EGFR(E746-A750DEL), EGFR(G719C), EGFR(G719S), EGFR(L747-E749DEL, A750P), EGFR (L747-5752 DEL, P753S), EGFR(L747-T751DEL,Sin), EGFR(L858R), EGFR(L861Q), EGFR(5752-1759DEL), EPHA5, EPHA6, ERBB2, ERBB4, ERK3, ERK4, FGR, FLT3(D835H), FLT3(D835Y), FLT3(ITD), FLT3(N841I), FRK, GAK, GCN2(KIN.DOM.2, S808G), HCK, IRAK3, JAK1(KIN.DOM.1), KIT, KIT(D816V), KIT(V559D), KIT (V559D,T670I), LCK, LOK, LTK, LYN, MAP3K3, MAP4K4, MAP4K5, MET, MINK, MKNK1, MKNK2, MST4, MYLK2, PDGFRB, PIM3, PKN2, PRKD1, PRKD2, PRKD3, PRKG1, RIPK2, RPS6KA4(KIN.DOM.2), SIK2, SLK, SNARK, SRC, STK36, TNIK, TNNI3K, TYK2(KIN.DOM.2).

Kinase Assays:

Assays were performed as described in Fabian et al. (2005) Nature Biotechnology, vol. 23, p. 329. Kinase-tagged T7 phage strains were grown in parallel in 24 or 96-well blocks in an E. coli host derived from the BL21 strain. E. coli were grown to log-phase and infected with T7 phage from a frozen stock (multiplicity of infection ~0.1) and incubated with shaking at 32° C. until lysis (~90 minutes). The lysates were centrifuged and filtered to remove cell debris. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions were assembled by combining phage lysates, liganded affinity beads, and test compounds in 1× binding buffer (20% SeaBlock, 0.17×PBS, 0.05% Tween 20, 6 mM DTT).

Test compounds were prepared as 40× stocks in DMSO and diluted into the aqueous environment. 2.5% DMSO was added to control assays lacking a test compound. All reactions were performed in polystyrene 96-well plates that had been pretreated with blocking buffer in a final volume of 0.04 ml. The assay plates were incubated at room temperature with shaking for 1 hour, long enough for binding reactions to reach equilibrium, and the affinity beads were washed four times with wash buffer (lx PBS, 0.05% Tween 20, 1 mM DTT) to remove unbound phage. After the final wash, the beads were resuspended in elution buffer (lx PBS, 0.05% Tween 20, 2 µM non-biotinylated affinity ligand) and incubated at room temperature with shaking for 30 minutes. The phage titer in the eluates was measured by quantitative PCR.

Results

The activity profile results are shown in Charts 1.1-1.6. Significant values are shaded. The kinases against which NRC-2694 (the compound of formula IA) is most active is indicated as (++) and where it has shown very little inhibiting effect is indicated as (--) in the following table.

| Kinase Activity Trends-NRC2694 (IA) | |
|---|---|
| (++) | (--) |
| ALK, | AKT1, AKT2, |
| BLK, | ASK1, AURKA$_1$, |
| CDK7, | BMPR$^1$A, BMPR$^2$, |
| CIT | CDK5, CDK8, |
| EGFR | EPHA2, ERK2, |
| ERK-3 | FGFR$^2$, FGFR3, |
| ERK-4 | GSK3B, LMK2, |
| FLT | MARK4, |
| GAK, | MEK3, MLK1, MST1, |
| LCK | MUSK, MYO3B, |
| LOK | p38, PCTK, P1K3CA, |
| MKNK | PKAC, PRKX, |
| PDGFR-B | RAF-1, RET, RPS6KA, |

| Kinase Activity Trends-NRC2694 (IA) | |
|---|---|
| (++) | (--) |
| PRKD | SRMS, STK16, |
| SLK | TRKA, ULK, |
| RIPK2 | YANK, ZAP70 |

Example 9

Anticancer Activity of the Compound of Formula (IA) in Pancreatic Cancer Models

In vivo anticancer activity of NRC-2694 (the compound of formula IA) for the treatment of Pancreatic Cancer in nude mice xenografts (Athymic nude mice).

Methodology

Athymic nude mice were implanted with $10\times10^6$ pancreatic cancer cells MIA PaCa-2 (ATCC #CRL1420). After tumor formation (~0.3-0.05 cm$^3$) mice were treated with study compounds with or without Gemcitabine. Tumor volume and animal activity were measured at regular intervals. At the termination of the experiment tumors were collected and fixed in 10% buffered formaldehyde for 12 hours and processed for paraffin embedding followed by sectioning. Tumor sections were immunoprobed for VEGF and Ki67 and percent expression determined with respect to controls.

| Study Design | | | | |
|---|---|---|---|---|
| Group # | Study Drugs | Dose (mg/kg) | Route | Number of Animals |
| 1 | Control | 0 | Oral | 5 Male + 5 Females |
| 2 | NRC 2694 | 20 | Oral | 5 Male + 5 Females |
| 3 | Erlotinib | 50 | Oral | 5 Male + 5 Females |
| 4 | Gemcitabine | 120 | i.p | 5 Male + 5 Females |
| 5 | NRC 2694 + Gemcitabine | 20 + 120 | Oral + ip | 5 Male + 5 Females |
| 6 | Erlotinib + Gemcitabine | 50 + 120 | Oral + ip | 5 Male + 5 Females |

Results

From the study conducted it was observed that NRC-2694 (the compound of formula IA) did cause the regression of pre-established subcutaneous pancreatic tumors in nude mice. Tumor regression caused by NRC2694 (the compound of formula IA) was similar to Erlotinib and Gemcitabine treatments. However, addition of Gemcitabine caused a greater than additive effect. Erlotinib hydrochloride (TARCEVA®) is an approved standard drug for the first-line treatment of patients with locally advanced, unresectable or metastatic pancreatic cancer, in combination with Gemcitabine. Gemcitabine (GEMZAR®) is indicated for the first line treatment for patients with locally advanced non-resectable or metastatic adenocarcinoma of the pancreas.

The tumor regression caused by treating with compound IA was superior to that caused by Erlotinib and Gemcitabine individually as well as in combination (FIG. 9). This observation was further confirmed in Immunohistochemical analysis (FIG. 10).

Example 10

Anticancer Activity of the Compound of Formula (IA) in HER2 Positive Breast Cancer In vivo anticancer activity of NRC-2694 (the compound of formula IA) for the treatment of HER2 Positive Breast Cancer in SCID mice xenografts.

Methodology

Animals were subcutaneously implanted with $2\times10^6$ cells. After the development of observable tumors drug treatment was initiated. As per IRB regulations no animals were allowed to bear tumors greater than 15 mm. Cell line: BT474/HTB20 human breast cancer cell line.

| | | Study Design | | |
|---|---|---|---|---|
| Group # | Study Drugs | Dose (mg/kg) | Route | Number of Animals |
| 1 | Control | 0 | Oral | 5 Male + 5 Females |
| 2 | NRC 2694 | 10, 20 and 40 (once a day) | Oral | 5 Male + 5 Females |
| 3 | Lapatinib | 30 and 100 (Twice a day) | Oral | 5 Male + 5 Females |

Results

NRC-2694 (the compound of formula IA) demonstrated a dose dependent increase in anti tumor activity in HER2 positive Breast cancer model. The tumor regression observed with NRC-2694 (the compound of formula IA) treated animals was superior to that of Lapatinib treated animals (FIG. 11). Lapatinib (TYKERB®) is a kinase inhibitor indicated in combination with Capecitabine for the treatment of patients with advanced or metastatic breast cancer whose tumors over express $HER^2$ and who have received prior therapy including an anthracycline, a taxane and trastuzumab. NRC-2694 (the compound of formula IA) was superior to Lapatinib, the established treatment option for HER2 expressing tumors, which was significant and unexpected.

Example 11

Anticancer Activity of the Compound of Formula (IA) in Erlotinib/Gefitinib Resistant NSCLC Model In vivo activity of NRC-2694 (the compound of formula IA) for the treatment of Erlotinib/Gefitinib resistant Non Small Cell Lung Cancer (NSCLC) in nude mice xenografts (athymic nude mice).

Methodology

Cells: H1975. Athymic nude mice, 5-8 weeks of age and weighing 20 to 25 g, were housed in the animal facility. H1975 cells were harvested from exponentially growing cultures, detached by brief trypsinization, washed twice in cold HBSS, resuspended in ice-cold HBSS, and implanted subcutaneously ($3\times10^6$ cells per mouse) into the dorsal hind flank. Treatment with the study drugs was initiated only after the tumor volume reached to 200-300 $mm^3$.

| | | Study Design | | |
|---|---|---|---|---|
| Group # | Study Drugs | Dose (mg/kg) | Route | Number of Animals |
| 1 | Control | 0 | Oral | 5 Male + 5 Females |
| 5 | NRC 2694 | 10 | Oral | 5 Male + 5 Females |
| 6 | NRC 2694 | 20 | Oral | 5 Male + 5 Females |
| 7 | NRC 2694 | 40 | Oral | 5 Male + 5 Females |
| 8 | Erlotinib | 100 | Oral | 5 Male + 5 Females |

Results

NRC 2694 (the compound of formula IA) demonstrated significant anticancer activity in animals implanted with Erlotinib/Gefitinib NSCLC resistant cells compared to Erlotinib or control. It showed dose dependent decrease in the tumor volume. Tumor remission was continued in animals treated with NRC 2694 (the compound of formula IA) even after withdrawing the study treatment (FIG. 12).

Drug resistance for treatment of non-small cell lung cancer (NSCLC) by approved drugs like Erlotinib (TARCEVA®) and Gefitinib (IRESSA®) is a clinical challenge posed and observed in recent times (Clin. Cancer. Res. 2006, 12(19): 5764-69; PLOS Medicine, March 2005, Online edition 0225-0235). The significant superior activity (250% reduction in tumor volume) observed with NRC-2694 (the compound of formula IA) was unexpected.

Example 12

NRC-2694 is Less Toxic Than Erlotinib in Swiss Albino Mice

This study determined that NRC-2694 (the compound of formula IA) is less toxic than erlotinib in Swiss albino mice. The maximum tolerated dose (MTD) of NRC-2694 is about twice that of erlotinib. The MTD of NRC-2694 is the same in mice and rats.

Materials and Methods

The method followed was as per the guidelines of FDA (Aug. 26, 1996).

Swiss Albino Mice 20 male and 20 female Swiss albino mice were randomly divided into four groups (G1-G4). Each group was 5 male and 5 female Swiss albino mice. Groups G2, G3 and G4 were treated with NRC-2694 monohydrochloride through oral route at the dose levels of 250, 500 and 1000 mg/kg body weight respectively. G1 was treated with placebo and served as a control. The oral formulation included 25 mg/mL of NRC-2694 that was administered in doses of 10 mL/kg body weight (b.wt) to each animal. Animals from the low dose group (G2-treated with 250 mg/kg b.wt) were administered the oral formulation as a single dose. The mid dose group animals (G3-treated with 500 mg/kg b.wt) were administered the dose formulation twice with a gap of approximately 1 hour. Animals from high dose group (G4-treated with 1000 mg/kg b.wt) received the dose formulation four times with a gap of approximately one hour.

Dose formulation analysis for test substance revealed 105.1, 105.74 and 105.76% recovery whereas dose formulation of placebo substance revealed 0% recovery of active ingredient.

At the end of observation period of 14 days, all surviving mice were sacrificed and subjected to gross pathological examinations.

Wistar Rats 20 male and 20 female Wistar rats were randomly divided in to four groups and dosed as described above for the mice.

Dose formulation analysis for test substance revealed 101.0, 102.84 and 103.56% recovery whereas dose formulation of placebo substance revealed 0% recovery of active ingredient.

Results

Mice: No mortality was observed in mice from the control as well as the treatment groups. Clinical signs of toxicity such as mild lethargy and piloerection were observed in high dose group after dosing during days 10 to 14. No significant alterations were observed in mean body weight and percent body weight when compared with their respective control groups. Gross pathological examination after day 14 did not reveal any lesions of pathological significance.

Rats: No mortality was observed in rats from the control as well as the treatment groups. In the high dose treated group (G4-1000 mg/kg body wt.) clinical signs of toxicity such as mild to severe lethargy (10/10), piloerection 10/10), chromodacryoorhea (10/10), weakness (1/10) and ptosis (4/10) were observed. Statistically significant reduction was observed in body weight and percent body weight change of mid and high dose treated group of rats on days 7 and 14. Reduction observed in the body weight and percent body weight change in high dose treated animals was considered as an effect of oral administration of NRC-2694 monohydrochloride. Gross pathological examination did not reveal any lesions of pathological significance, except minimal uterus distension in two female rats. This lesion was physiological or cyclic in nature and could be considered as a spontaneous finding.

Conclusions

Mice: Based on the findings of this study, it was concluded that the test substance NRC-2694 monohydrochloride did not produce any toxic signs or mortality when administered through oral gavage at the dose level of 250 mg/kg body weight (low dose) and 500 mg/kg (mid dose). At 1000 mg/kg (high dose) the NRC-2694A blend produced signs of lethargy and piloerection in all animals without any mortality. The MTD of NRC-2694 monohydrochloride by acute oral gavage in Swiss albino mice was 1000 mg/kg body weight under the condition and the procedures followed in the present study.

Under our laboratory condition, the MTD of Erlotinib HCl was recorded to be 500 mg/kg, when given orally to Swiss albino mice. Thus, NRC-2694 is advantageously significantly less toxic than Erlotinib HCl in mice.

Rats: Based on the findings of this study, it was concluded that the test substance NRC-2694A blend did not produce any major toxic signs or mortality when administered through oral gavage at the dose level of 250 mg/kg body weight (low dose) and 500 mg/kg body weight (mid dose). However, at the dose level of 1000 mg/kg body weight (high dose), the NRC-2694A blend produced marked toxic signs with reduction in body weight but devoid of any pathological lesions and mortality. Based on the above study, the MTD of NRC-2694A blend by acute oral gavage in Wistar rats is considered as 1000 mg/kg body weight under the condition and the procedures followed in the present study.

Example 13

NRC-2694 is Less Toxic than Erlotinib in Beagle Dogs

This study determined that NRC-2694 (the compound of formula IA) is less toxic than erlotinib in beagle dogs. The no observed adverse effect level (NOAEL) of NRC-2694 is about twice that of erlotinib.

Materials and Methods

The methods followed were as per CPMP/SWP/1042/99 (July 2000) and ICH S3A (March (1995)) guidelines. Prior to the 30 day repeated dose study, a dose range finding study was conducted, which included single dose MTD study followed by a 10 day repeated dose study. For the single dose MTD study, two dogs (1 male and 1 female) of beagle breed, obtained from Marshall's Farm, China, were used. The route of dosing was oral, by gelatin capsule. Based on the results of the dose range finding study, doses for the 30 days study were selected.

The 30 day repeated dose study employed 12 male and 12 female dogs (Marshall's Farm, China). The dogs were acclimatized for a minimum period of 2 weeks and randomly divided into four main groups (G1-G4), each group comprising of 3 dogs per sex. The animals were dosed orally with capsules of NRC-2694A for a period of 30 consecutive days at dose levels of 10 mg/kg b.wt/day (G2-low dose), 20 mg/kg b.wt/day (G3-mid dose) and 40 mg/kg b. wt/day (G4-high dose). However, the high dose was subsequently decreased to 30 mg/kg b.wt/day. The control group (G1-0 mg/kg b. wt/day) animals were dosed by oral capsule with placebo.

Each dog was observed for visible signs of reaction once daily and for mortality and morbidity twice daily throughout the study period. The study also tracked body weight (weekly), food consumption (daily), ophthalmological status (start and end), hematological and biochemical analyses (start and end), toxicokinetics analysis of plasma (start and end). At the end of the study, all dogs were euthanized by a humane and accepted procedure, subjected to a gross postmortem examination, organ weights (absolute and relative) were determined, and histopathological examination was carried out.

Results

No symptoms of toxicity observed in the low dose (G2) and control (G1) groups. The toxicokinetic parameters viz. Lambda z, HL Lambda z, $T_{max}$, $C_{max}$, $AUC_{00}$ of NRC-2694 monohydrochloride on Day 1 was calculated separately for male and female dogs by using WinNonlin version 5.2 software. There was a dose-dependent change in the $C_{max}$ of NRC-2694 monohydrochloride at the three dose levels in both male and female dogs. The median $T_{max}$ for attaining $C_{max}$ at three dose levels (10, 20 and 40 mg/kg) on day 1 were 2, 3, 2 hr in male and 2, 4, 4 hr in female, respectively. The median $T_{max}$ for attaining $C_{max}$ at two dose levels (10 and 20 mg/kg) on day 30 were 2 and 3 hr in male and 2 and 4 hours in female, respectively.

Conclusion

Based on the results of this study, it was concluded that the no observed adverse effect level (NOAEL) of NRC-2694 monohydrochloride in beagle dogs dosed over a period of 30 days is 10 mg/kg b.wt/day when administered orally by capsule. The corresponding value for Erlotinib HCl is 5 mg/kg b.wt/day. Thus, NRC-2694 is advantageously significantly less toxic than Erlotinib HCl in beagle dogs.

Example 14

NRC-2694 is not Mutagenic in the Ames Test

This study determined that NRC-2694 (the compound of formula IA) is not mutagenic in the Ames test.

Materials and Methods

The present study was conducted by the direct plate incorporation method with five tester strains of *Salmonella typhimurium* (TA 98, TA 100, TA 102, TA 1535 and TA 1537). NRC-2694 was tested at the doses of 1.2500, 0.3955, 0.1251, 0.0396 and 0.0125 mg/plate. Simultaneously, negative control cultures received DMSO and the respective positive controls received the mutagens 2-Amino anthracene, 2-Nitrofluorene, Sodium azide, 9-Aminoacridine and Mitomycin C (Sigma, St. Louis). In order to study the role of metabolic activation, cultures were incubated both with and without S9 mixture. The induction of Histidine positive colonies was computed and results were statistically treated for comparison.

Results and Conclusion

The study indicated lack of statistically significant induction of His revertant colonies using NRC-2694 in any of the tester strains either with or without S9 addition in the culture when compared to positive and negative controls. Based on the above results, it was concluded that the NRC-2694 monohydrochloride was non-mutagenic according to the Ames bacterial reverse mutation assay.

Example 15

NRC-2694 Lacks Neurotoxicity in the Functional Observational Battery

This study determined that NRC-2694 (the compound of formula IA) showed no evidence of neurotoxicity toward the central and peripheral nervous system in Wistar rats using the functional observations battery (FOB) test.

Materials and Methods

The study was conducted in accordance with "S7A Safety Pharmacology Studies for Human Pharmaceuticals, ICH" July 2001, and as per this study protocol. The FOB assessed the effect of NRC-2694 monohydrochloride on the central and peripheral nervous systems in Wistar rats. Rats that had been fasted for 16 to 18 hours (access to water was not interrupted) were dosed with the compound or water. The rats were administered the compound in an aqueous formulation at three levels, 75, 125 and 250 mg/kg b.wt, as a single oral dose by gavage. The control group received water. The rats were subjected to the FOB 60-120 min. after drug administration.

Animals were subjected to the FOB one at a time except for the multiple activity cage where four animals were placed in four different cages simultaneously. Once complete, the animals were returned to their home cage and the cage placed back on the stand.

Results and Discussion

The functional observational battery tests carried out did not show any adverse effects at the tested doses. NRC-2694A was well tolerated at the given doses having no influence on any of the parameters of the FOB 60-120 minutes post treatment.

The FOB can be employed to assess multiple neurobiological domains including neuromuscular (weakness, in coordination, gait and tremor), sensory (audition, vision and somatosensory), and autonomic (pupil response and salivation) functions. The measures of a neuro behavioral screening battery have been divided into specific functional domains. For example, Lacrimation, salivation, pupil response, palpebral closure, defecation and urination are measures of some aspects of the autonomic system. Similarly the neuro muscular domain can be assessed based on the gait/mobility score, landing foot splay, grip strength and righting reflex; sensorimotor domain based on response to tail pinch and click/touch/approach response; CNS excitability domain based on ease of removal and handling of the animal, clonic/tonic movements, arousal and vocalization; CNS activity domain based on home cage posture, palpebral closure, rearing and motor activity and finally the physiological domain is assessed based on the body weight, body temperature and piloerection.

Example 16

NRC-2694 Lacks Toxicity Against Respiratory Function

This study determined that NRC-2694 (the compound of formula IA) lacks toxicity against respiratory function in Wistar rats.

Materials and Methods

This study evaluated the effect of NRC-2694A monohydrochloride on respiratory function in conscious Wistar rats following administration of a single dose using a whole body plethysmograph. The study was conducted in accordance with "S7A Safety Pharmacology Studies for Human Pharmaceuticals, ICH" issued July 2001. The study used a parallel design with one vehicle and three test item treated groups. NRC-2694 monohydrochloride was administered orally at the doses of 75, 125 and 250 mg/kg body weight. Male Wistar rats were placed in plethysmography chambers and baseline respiratory parameters were recorded for 30 minutes. Following drug administration respiratory parameters were recorded continuously for 3 hours.

Results

At the tested doses NRC-2694 monohydrochloride did not influence any of the observed parameters: respiratory rate, tidal volume, minute volume, and Penh.

Example 17

NRC-2694 Lacks Toxicity Against Cardiovascular Function

This study determined that NRC-2694 (the compound of formula IA) lacks toxicity against cardiovascular function in beagle dogs.

Materials and Methods

This study evaluated the effect of orally administered NRC-2694 monohydrochloride on cardiovascular parameters in telemetered male Beagle dogs. The study was conducted in accordance with ICH "S7A Safety Pharmacology Studies for Human Pharmaceuticals, Note for Guidance on Safety Pharmacology Studies for Human Pharmaceuticals, July 2001". The doses tested were 0, 15, 30 and 60 mg/kg b.wt. given orally by gelatin capsule. Four male Beagle dogs, each implanted with a TL1IM2-D70-PCT transmitter (Data Sciences International, USA), were used for the study. During the study, the dogs were administered 4 oral treatments representing placebo and all test substance treatment groups with a three day (~72 hour) wash-out period between each administration, using a Latin square cross-over design.

On dosing days, the telemetered dogs were observed once before commencement of data collection, continuously through 2 hours post-dose remotely and −8 hours post-dose for changes in behaviour. Cardiovascular parameters (systolic, diastolic and mean blood pressure, pulse pressure and heart rate) were recorded continuously for ~60 minutes before dosing and up to 24 hours after dosing. Systolic, diastolic and mean blood pressures, pulse pressure and heart rate were obtained from the femoral artery waveform. Electrocardiograms were recorded continuously for ~60 minutes before dosing and up to 24 hours after dosing. Electrocardiograms were obtained from subcutaneously placed biopotential leads in a Lead II configuration. Heart rate and QT intervals were determined from the ECG's.

Results

When administered orally to male Beagle dogs, NRC-2694 monohydrochloride had no significant negative effects on cardiovascular parameters (systolic, diastolic and mean blood pressure, pulse pressure, heart rate, or QT and corrected QT (QTcf) intervals) at the doses tested. The no observed effect level was 60 mg/kg b.wt.

Example 18

NRC-2694 is Safe in a Test of Cardiac Risk Assessment

This study determined that NRC-2694 (the compound of formula IA) is safe in a recombinant cell system used as an index of QT interval prolongation for cardiac risk assessment.

Materials and Methods

The effect of NRC-2694 monohydrochloride on the potassium selective Ikr (tail) current (the rapid component of the delayed rectifier current) was investigated using Chinese hamster ovary (CHO) cells stably transfected with hERG (human ether-a go-go related gene) employing the whole cell patch-clamp technique. Blockade of the Ikr potassium current is considered to constitute an index of QT interval prolongation for cardiac risk assessment. The test was conducted according to S7B: The Nonclinical Evaluation of the Potential for Delayed Ventricular Repolarization (QT Interval Prolongation) By Human Pharmaceuticals. ICH May 2005

This CHO cells stably transfected with hERG were from Flyion GmBH (Germany). Stock cultures of hERG-TRex-CHO cells were stored as frozen permanents in liquid nitrogen. The test compound was evaluated at 10 μM in 0.1% DMSO (v/v). Propafenone (Sigma, St. Louis) at 10 μM was the positive control. The vehicle control was 0.1% (v/v) DMSO in EC solution.

The selection medium was F-12 (Ham)+GlutaMAX, Ph 7.2, 10% FBS, Penicillin (100 U/mL), Streptomycin (100 μg/mL), Blasticidin S HCL (30 μg/mL) and Hygromycin B (400 μg/mL). The growth medium was F-12 (Ham)+GlutaMAX, 10% FBS, Penicillin (100 U/mL) and Streptomycin (100 μg/mL). The induction medium was F-12 (Ham)+GlutaMAX, 10% FBS, Penicillin (100 U/mL) and Streptomycin (100 μg/mL) and Doxycycline (3 μg/mL). The cell dissociation solution was 0.05% Trypsin-EDTA. The extracellular solution (and robot medium) was NMDG 145 mM, KCl 5 Mm, $MgCl_2(H_2O)_6$ 1 Mm, HEPES 10 mM, Glucose 10 mM, at pH 7.4. The intracellular solution was $KMeSO_3$ 115 mM, $MgCl_2(H_2O)_6$ 5 mM, HEPES-KOH 10 mM, EGTA 5 mM, $K_2ATP$ 5 mM, at pH 7.2.

Results and Discussion

The test compound was evaluated at 10 μM where it showed ~42% inhibition of hERG current. This suggests that NRC-2694, in the experimental context of this study, was an inhibitor of the hERG channel. The positive control, propafenone, caused ~69% inhibition at 10 μM, indicating the sensitivity of the test system. The tail current mainly reflects the open channel state and is the appropriate index for hERG channel evaluation. Inhibition of the hERG channel can lead to delayed repolarization, which can manifest itself as a prolongation of the QT-interval.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A method of inhibiting the growth of a tumor cell in wherein the tumor cell is a HER2 positive breast cancer cell, the method comprising administering to a subject in need thereof an effective amount of a quinazoline derivative of formula (IA):

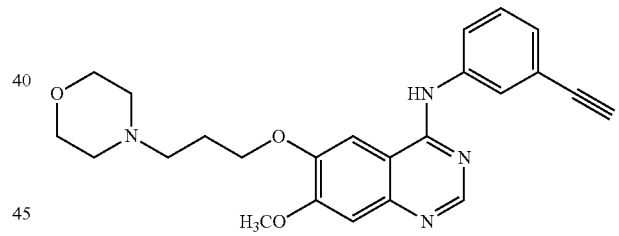

or a pharmaceutically acceptable salt thereof.

2. The method of claim 1, wherein the pharmaceutically acceptable salt is a monohydrochloride, a dihydrochloride, or a mixture thereof.

* * * * *